US008124413B2

(12) United States Patent
Stanley et al.

(10) Patent No.: US 8,124,413 B2
(45) Date of Patent: Feb. 28, 2012

(54) THERMOCYCLER AND SAMPLE PORT

(75) Inventors: Keith Stanley, Caringbah (AU); John Corbett, Mortlake (AU)

(73) Assignee: Corbett Life Science Pty Ltd, New South Wales (AU)

(*) Notice: Subject to any disclaimer, the term of this patent is extended or adjusted under 35 U.S.C. 154(b) by 46 days.

(21) Appl. No.: 12/162,942

(22) PCT Filed: Feb. 2, 2007

(86) PCT No.: PCT/AU2007/000108

§ 371 (c)(1),
(2), (4) Date: May 14, 2009

(87) PCT Pub. No.: WO2007/087690

PCT Pub. Date: Aug. 9, 2007

(65) Prior Publication Data

US 2009/0220966 A1 Sep. 3, 2009

(30) Foreign Application Priority Data

Feb. 2, 2006 (AU) ................................ 2006900504

(51) Int. Cl.

| | |
|---|---|
| ***G01N 35/08*** | (2006.01) |
| ***G01N 1/10*** | (2006.01) |
| ***G01N 21/00*** | (2006.01) |
| ***G01N 31/00*** | (2006.01) |
| ***G01N 33/00*** | (2006.01) |
| ***B01L 3/00*** | (2006.01) |
| ***B01L 99/00*** | (2010.01) |

(52) U.S. Cl. .............. 436/53; 436/180; 422/81; 422/82; 422/500

(58) Field of Classification Search .................... 422/82; 436/52–53
See application file for complete search history.

(56) References Cited

U.S. PATENT DOCUMENTS

| | | | | |
|---|---|---|---|---|
| 4,015,938 | A * | 4/1977 | Jay | 73/864.22 |
| 4,683,195 | A | 7/1987 | Mullis et al. | |
| 4,683,202 | A | 7/1987 | Mullis | |
| 4,800,159 | A | 1/1989 | Mullis et al. | |
| 4,889,818 | A | 12/1989 | Gelfand et al. | |
| 4,965,188 | A | 10/1990 | Mullis et al. | |
| 4,997,627 | A | 3/1991 | Bergkuist et al. | |
| 5,023,171 | A | 6/1991 | Ho et al. | |
| 5,066,584 | A | 11/1991 | Gyllensten et al. | |
| 5,075,216 | A | 12/1991 | Innis et al. | |

(Continued)

FOREIGN PATENT DOCUMENTS

| | | |
|---|---|---|
| CA | 1043128 | 11/1978 |

(Continued)

OTHER PUBLICATIONS

International Search Report No. PCT/EP2007/000108, dated Apr. 27, 2007, 4 pgs.

(Continued)

*Primary Examiner* — Jill Warden
*Assistant Examiner* — Charles D Hammond
(74) *Attorney, Agent, or Firm* — Baker Donelson Bearman, Caldwell & Berkowitz, PC

(57) ABSTRACT

The invention relates to continuous flow systems, in particular thermocyclers for the automated and continuous cycling of fluid between a plurality of temperature zones in the amplification of nucleic acids. The invention also relates to an improved sample port for introducing a volume of a liquid sample into a continuous flow system.

12 Claims, 20 Drawing Sheets

U.S. PATENT DOCUMENTS

| | | | | |
|---|---|---|---|---|
| 5,091,310 | A | 2/1992 | Innis | |
| 5,104,792 | A | 4/1992 | Silver et al. | |
| 5,270,183 | A | 12/1993 | Corbett et al. | |
| 5,443,791 | A | 8/1995 | Cathcart et al. | |
| 5,656,493 | A | 8/1997 | Mullis et al. | |
| 5,827,480 | A | 10/1998 | Haff et al. | |
| 6,656,724 | B1 | 12/2003 | Heimberg et al. | |
| 6,887,429 | B1 | 5/2005 | Marshall et al. | |
| 2001/0041357 | A1 * | 11/2001 | Fouillet et al. | 435/91.1 |
| 2002/0104578 | A1 * | 8/2002 | Kubokawa | 141/39 |
| 2004/0022686 | A1 * | 2/2004 | Charles et al. | 422/82.08 |
| 2005/0066750 | A1 | 3/2005 | Bigalke | |

FOREIGN PATENT DOCUMENTS

| | | |
|---|---|---|
| WO | WO 03/016558 | 2/2003 |

OTHER PUBLICATIONS

Supplementary European Search Report of EP07701440, dated May 27, 2010 (2 pages).

* cited by examiner

THERMOCYCLER AND SAMPLE PORT

CROSS REFERENCE TO RELATED APPLICATIONS

This application is a §371 National Stage Application of PCT/EP2007/000108, filed Feb. 2, 2007, which claims priority to Australian Application 2006900504, filed Feb. 2, 2006, the content of which is incorporated by reference.

BACKGROUND OF THE INVENTION

1. Field of the Invention

The present invention relates to thermocyclers and in particular to thermocyclers for the automated and continuous cycling of fluid between a plurality of temperature zones.

The invention has been developed primarily for use as a thermocycler for nucleic acid amplification and will be described hereinafter with reference to this application. However, it will be appreciated that the invention is not limited to this particular field of use.

The present invention also relates to a continuous flow system and in particular to a sample port for introducing a volume of a liquid sample into a continuous flow system. However, it will be appreciated that the invention is not limited to this particular field of use.

2. Description of Related Art

Any discussion of the prior art throughout the specification should in no way be considered as an admission that such prior art is widely known or forms part of the common general knowledge in the field.

Systems which require multiple or cyclic chemical reactions to produce a desired product often require careful temperature control, and reproducible and accurate control over the time the reaction is held at temperature. Such reactions include, for example, nucleic acid amplification reactions such as the polymerase chain reaction (PCR) and the ligase chain reaction (LCR).

PCR is a technique involving multiple cycles that results in the geometric amplification of certain polynucleotide sequences each time a cycle is completed. The technique of PCR is well known and is described in many books, including, *PCR: A Practical Approach* M. J. McPherson, et al., IRL Press (1991), *PCR Protocols: A Guide to Methods and Applications* by Innis, et al., Academic Press (1990), and *PCR Technology: Principals and Applications for DNA Amplification* H. A. Erlich, Stockton Press (1989). PCR is also described in many US patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584.

The PCR technique typically involves the step of denaturing a polynucleotide, followed by the step of annealing at least a pair of primer oligonucleotides to the denatured polynucleotide, i.e., hybridizing the primer to the denatured polynucleotide template. After the annealing step, an enzyme with polymerase activity catalyzes synthesis of a new polynucleotide strand that incorporates the primer oligonucleotide and uses the original denatured polynucleotide as a synthesis template. This series of steps (denaturation, primer annealing, and primer extension) constitutes a PCR cycle.

As cycles are repeated, the amount of newly synthesized polynucleotide increases geometrically because the newly synthesized polynucleotides from an earlier cycle can serve as templates for synthesis in subsequent cycles. Primer oligonucleotides are typically selected in pairs that can anneal to opposite strands of a given double-stranded polynucleotide sequence so that the region between the two annealing sites is amplified.

Denaturation of DNA typically takes place at around 90 to 95° C., annealing a primer to the denatured DNA is typically performed at around 40 to 60° C., and the step of extending the annealed primers with a polymerase is typically performed at around 70 to 75° C. Therefore, during a PCR cycle the temperature of the reaction mixture must be varied, and varied many times during a multicycle PCR experiment.

A number of thermal "cyclers" used for DNA amplification and sequencing are disclosed in the prior art in which one or more temperature controlled elements or "blocks" hold the reaction mixture, and wherein the temperature of the block is varied over time. These devices suffer the drawback that they are slow in cycling the reaction mixtures and temperature control is less than ideal. In an effort to overcome the need to cyclically raise and lower the temperature of the heating blocks, others have devised apparatus known in the art as a thermocycler. In this apparatus, multiple temperature controlled blocks are kept at different desired temperatures and a robotic arm is utilized to move reaction mixtures from block to block. Typical thermocycler systems are disclosed in U.S. Pat. Nos. 5,443,791; 5,656,493 and 6,656,724. However, as will be appreciated, these systems suffer from their own set of drawbacks. For example, they have a relatively limited throughput, they are physically large, prone to break down, expensive and require constant routine maintenance.

Difficulties encountered with these aforementioned devices were in part addressed by the invention disclosed in U.S. Pat. No. 5,270,183. In essence, that invention was directed to the reactants travelling through a continuous tube which was subjected to varying temperatures by coiling the tube around substantially drum shaped bodies held at varying temperatures. In order to prevent cross contamination between samples, the reaction mixture was injected into a stream of carrier fluid which separated individual reaction mixtures and passed through two or three separate heating zones. The carrier fluid and reaction mixture are immiscible such that each sample is cleanly separated from the preceding and following sample by segments of carrier fluid. This arrangement allows sequential processing of a number of samples. However, this device has drawbacks, for example since the heating zones are spatially separated it is not convenient to conduct real-time monitoring of the course of a reaction. In addition, having heating zones separated from each other physically tends to be cumbersome.

An advance over the invention disclosed in U.S. Pat. No. 5,270,183 is described in WO 03/016558 in which a single drum shaped body is longitudinally divided to provide at least two segments which are able to be heated to different temperatures such that the body may have peripheral surfaces of different temperatures. As the reactants travel through the continuous tube coiled around the body the reactants are subjected to alternating temperatures. However, the problem with such a thermocycler is that it is difficult to obtain a sufficiently rapid readout of data using the linear tracking device, which scans the periphery of the drum.

With respect to continuous flow systems and apparatus generally, including thermocyclers described above, they are typically operated under positive pressure and require pumps for pumping a carrier fluid through a continuous tube/conduit such as a reaction tube. Typically, these pumps are high or very high pressure pumps. Accordingly, these prior art continuous flow apparatus require specialised high-pressure injection ports for delivering a liquid sample into the stream of carrier fluid being pumped under high pressure through the tube. These high-pressure injection ports suffer a variety of drawbacks. However, the major drawback is their propensity for cross contamination between samples such as for example contamination of samples during loading, largely due to the septum-needle arrangement for injecting the sample, or between samples as they travel down the tubing.

Thus there still remains a need for improved continuous flow systems, including thermocycler devices as described herein, as well as sample handling and delivery means.

It is an object of the present invention to overcome or ameliorate at least one of the disadvantages of the abovementioned prior art, or to provide a useful alternative.

SUMMARY OF THE INVENTION

Certain preferred embodiments of the present invention provide a thermocycler which is able to vary in a cyclical or progressive manner the temperature of a fluid in a tube, or is able to maintain the fluid at a constant temperature, with improved control over the temperature at which the fluid is maintained compared to prior art devices, and provide improved means for monitoring reactions taking place in the tube. Other embodiments of the invention provide a sample port for use with continuous flow systems, particularly those in which samples are drawn through a column or a tube rather than pumped through under pressure.

BRIEF DESCRIPTION OF THE DRAWINGS

A preferred embodiment of the invention will now be described, by way of example only, with reference to the accompanying drawings in which.

DETAILED DESCRIPTION OF A PREFERRED EMBODIMENT

Figure 1:
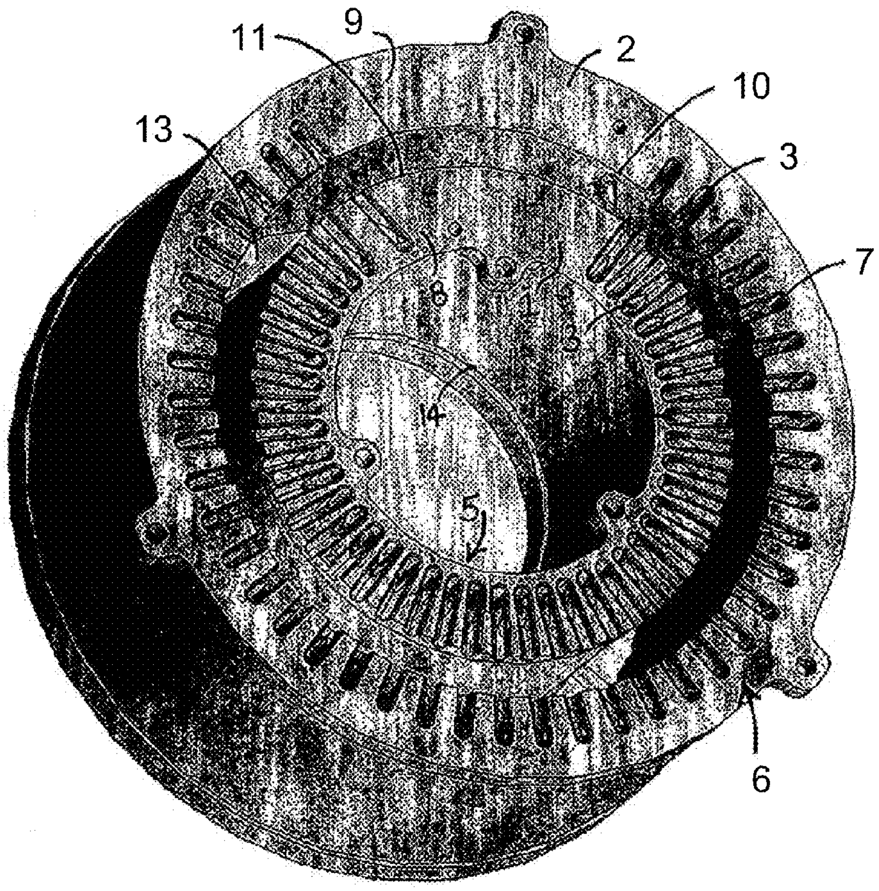
FIG. 1 is a perspective top view of a thermocycler according to the invention.

According to a first aspect the present invention provides a thermocycler comprising a plurality of nested heat exchangers for independently maintaining a predetermined temperature thereby to define a corresponding plurality of temperature zones; said heat exchangers adapted to receive a reaction tube such that said reaction tube is in heat transfer communication with said heat exchangers, whereby a fluid passing through a reaction tube engaged with said heat exchangers passes cyclically through the temperature zones.

According to a related aspect the present invention provides a thermocycler including a pair of nested inner and outer heat exchangers, wherein each heat exchanger includes a plurality of tunnels and is adapted to maintain a predetermined temperature thereby to define a plurality of temperature zones; and a reaction tube engaged with the tunnels for thermal contact with the temperature zones, whereby the reaction tube is alternatingly threaded through successive tunnels of each heat exchanger such that a fluid passing through the reaction tube cyclically passes through the temperature zones.

The heat exchangers are preferably arranged concentrically although this type of arrangement is not critical to the design or functionality of the thermocycler.

Preferably the tunnels run parallel to the axis of the concentric heat exchangers. In a preferred embodiment the tunnels are open on at least one face to provide a surface groove for holding the reaction tube substantially on the surface of the heat exchanger. Alternatively, the tunnels are a partially enclosed surface groove thereby allowing the reaction tube to be "snap-locked" therein.

The outer heat exchanger may have a ring structure having a transverse cross-section which is substantially circular, but this type of arrangement is again not critical to the design or functionality of the thermocycler. The inner heat exchanger may be either tubular or a solid rod or block. Optionally the heat exchangers are toroidal.

The inner of the heat exchanger rings may include at least one slot for optically monitoring the reaction tube.

In one embodiment, the end surfaces of the inner heat exchanger lie substantially flush with the corresponding end surfaces of the outer heat exchanger. However, in other embodiments one or both end surfaces of the inner heat exchanger may be axially spaced from the corresponding end surface of the outer heat exchanger.

The predetermined temperature of each heat exchanger may be maintained using a variety of heating and/or cooling means. Preferably the heating and/or cooling means are chosen from a resistance wire and a Peltier device. For a nucleic acid amplification the predetermined temperatures may be about 95° C., about 60° C., or about 72° C. It will be understood of course that any range of temperatures can be easily selected and maintained for any particular section of the heat exchangers. The heat exchangers are preferably maintained at a constant temperature. However, the heat exchangers may be adapted to maintain an axially varying temperature profile, which for example may be from about 55° C. to about 95° C. However it will be appreciated that any varying temperature profile may be chosen according to the particular application.

In a particular embodiment of the invention each heat exchanger preferably includes an array of mutually opposed reaction tube alignment formations on their respective end surfaces. The formations may be longitudinally recessed radially extending slots for positioning the tube such that the tube sits substantially flush with each end surface of each heat exchanger. The formations are disposed on the inner peripheral edge of the outer heat exchanger and on the outer peripheral edge of the inner heat exchanger.

Preferably the tunnels in each heat exchanger are radially equidistant and disposed in a spaced array. Any number of tunnels or grooves may be provided in/on each heat exchanger, however a typical number of tunnels or grooves is between about 15 and 75. Preferably the number of tunnels is 40 to 50.

Preferably the reaction tube is substantially transparent and formed from an inert resilient material such as Teflon or Tefzel or similar material. Preferably the internal surface of the tube is hydrophobic. The tubing should be selected for close fitting relationship with the tunnels for improved thermal/heat-transfer communication thereby to conduct heat from the heat exchangers to the fluid being pumped through the reaction tube. The reaction tube arrangement with respect to the heat exchangers is such that a continuous flow configuration can be achieved. Preferably the reaction tube is removable and replaceable.

In another embodiment of the present invention the outer and inner heat exchangers may be sub-divided into a plurality of discrete axially spaced heat exchangers, each heat exchanger being adapted to maintain a temperature which might be the same or different from the adjacent heat exchanger. Using this embodiment the invention can be programmed to perform 2 step, 3 step or 4 step reactions with a residence time at each temperature varied according to the number of heat exchangers at that given temperature. Contiguous blocks of heat exchangers may be used to maintain a constant temperature for an extended time. For example, two of the four heat exchangers can be maintained at about 70° C. to provide a longer extension reaction than denaturation or annealing. Optionally the arrangement of high and low temperature heat exchangers can be rearranged so that fluorescent measurement can take place at different points of the thermal cycle. Further still, the heat exchangers may be divided any number of times to provide any number of temperature zones, however it will be appreciated that 4 temperature zones is sufficient for most PCR/LCR reactions.

The thermocycler may also include one or more further heat exchangers surrounding the outer heat exchanger for providing further temperature zones.

Preferably the reaction tube includes an inlet port for introducing fluids into the reaction tube and a delivery device for maintaining a flow through the reaction tube. In use, the delivery device maintains the flow through the reaction tube under pressure. Preferably the pressure is between about 70 to about 700 kPa. Back pressure is typically applied at the end of the reaction tube at between about 30 and 70 kPa. In alternative embodiments of the present invention flow of liquid through the thermocycler is maintained by negative pressure applied to the exit of the flow tube. This has the advantage of allowing samples to be introduced at atmospheric pressure using a zero contact and contamination free method (see hereinafter).

Preferably the fluids include a sample to be analysed or reacted, reagents to be used in the analysis or reaction, and a carrier fluid. In one embodiment a sample is separated from a following sample by the carrier fluid to substantially prevent contamination between samples, i.e. carrier-sample-carrier configuration. However, in an alternative embodiment, a washing fluid can also be interspersed between samples, i.e. carrier-wash-carrier-sample-carrier-wash-carrier configuration. The preferred carrier fluid is silicon oil, or any synthetic combined oil which is devoid of biological contaminants. Preferably the wash fluid is pure water. In embodiments in which the thermocycler is used for nucleic acid amplification the carrier fluid should be devoid of nucleic acids such as RNA or DNA. Preferably the sample to be analysed or reacted is a nucleic acid such as DNA or RNA containing sample. Other components of the sample will typically include oligonucleotide primers, deoxyadenosine triphosphate (dATP), deoxycytidine triphosphate (dCTP), deoxyguanosine triphosphate (dGTP), deoxythymidine triphosphate (dTTP), and at least one of a thermostable DNA polymerase, enzymatically active fragments thereof, an enzymatically active derivative thereof and a reverse transcriptase.

Preferably the time the sample is maintained at the predetermined temperature is pre-selectable by choice of flow rate, the relative axial length of the heat exchangers and/or the diameter of the reaction tube. In an embodiment of the invention which makes use of the thermocycler for nucleic acid amplification, the timing is sufficient such that the following reactions take place:

(a) denaturation of the DNA into its component strands;
(b) annealing of the oligonucleotide primers to complementary sequences in the DNA; and
(c) synthesis of new DNA strands;

Preferably these steps are repeated until a desired level of amplification has been achieved.

The thermocycler may also include a pre-coil for denaturing the sample, wherein the sample is typically denatured for between about 2 to 10 minutes.

Preferably a marker reagent for monitoring a reaction in the reaction tube is also added to the reaction fluid and/or sample. The marker reagent can be suitably chosen from the group consisting of: a fluorescent dye, an intercalating dye, a chromogenic substrate, or oligonucleotide probes covalently bound to fluorescent moieties.

In other embodiments the thermocycler may include a further C-shaped heat exchanger surrounding the outer heat exchanger for providing a DNA-melt analysis on the amplified product. The circumferential gap of the C-shaped heat exchanger may be between about 20 to about 100°, however the circumferential gap of the C-shaped heat exchanger is preferably about 20°. The C-shaped heat exchanger may include a circumferentially varying temperature profile which could vary from about 70° C. to about 95° C. However, it will be appreciated that any temperature profile could be chosen according to the particular application. The reaction tube may be disposed in a single loop around the upper or lower end face of the C-shaped heat exchanger such that as the sample migrates around the circumference it is exposed to the varying temperature profile. Optionally the fluorescence of the sample is detected as it migrates around the loop so that a melt profile can be determined. However, in alternative embodiments the C-shaped heat exchanger includes a groove for holding the reaction tube wherein the groove is disposed on of the side of the heat exchanger. Melt detection studies are typically performed in between about 1 to 20 minutes, preferably 2 minutes.

In yet another embodiment, a post-melt on the amplified product may be performed on a C-shaped heat exchanger in which the reaction tubing is wound around the heat exchanger and wherein the temperature at each end of the C-shaped heat exchanger is maintained at a different temperature. Each turn of the tubing on such a melt device would thus be at a discrete temperature giving as many measurements in the melt determination as there are turns of tubing on the heat exchanger. The tube could also be wound around the inside perimeter of the C shaped exchanger, so that with a high speed spinning scanner the melt resolution would be based on the scan speed and not the number of turns around the heat exchanger. This approach would also provide a much faster melt time given the tube length would be significantly (e.g. more than 10 times) shorter.

The thermocycler may further include a scanning detector for monitoring the course of a reaction occurring in the reaction tube. Preferably the course of the reaction is measured by fluorescence. In one embodiment the scanning detector includes a rotatable unit axially mounted above (or below) the thermocycler heat exchanger rings for directly measuring the tube in the circumferential gap between the inner and outer heat exchangers. The unit may include at least one detection channel having a source of incident light and a detector. For example, the source of incident light may be a mercury arc lamp with suitable filters and the source of incident light may be a LED or a laser. Preferably the unit includes four detection channels corresponding to blue, green, yellow and red incident light. Further, the unit preferably further includes at least one "melting" detection channel for detecting a melting profile when the C-shaped heat exchanger is installed. Preferably the rotatably unit rotates at greater than 500 rpm. It will be appreciated that the aforementioned scanning detector requires only one excitation and one detector port per wavelength.

In another embodiment, the scanning detector may comprise an axially rotatable 45° mirror centrally disposed within the inner heat exchanger thereby to detect the course of a reaction through the slot. In this embodiment, the scanning detector directs incident light along the axis of the thermocycler which is reflected by the mirror onto each "turn" of the reaction tube as the mirror completes a single rotation such that the reaction tube can be continuously scanned and each reaction detected as it passes through the rotating light beam. The epifluorescent light may be channeled back down the same optical path and passed through a dichroic mirror to a detector. The fluorescence detection may be simultaneous with illumination or delayed using alternate illumination and detection scans.

It will be appreciated that these detectors are capable of detecting the course of a reaction occurring in the reaction tube in real-time due to the rapid data acquisition.

In other embodiments, a plurality of detectors are mounted above the circumferential gap between the heat exchangers, wherein an equal number of detectors are provided for the number of exposed reaction tubes. Alternatively, the detectors measure groups or pairs of reaction tubes. Any type of detector is suitable, including cameras, photodiodes and photomultipliers.

According to a second aspect the present invention provides a method of amplifying a nucleic acid in a PCR or LCR format using the thermocycler device of the first aspect.

According to a third aspect the present invention provides a method of performing a nucleic acid melt detection assay using the thermocycler device of the first aspect.

According to a fourth aspect the present invention provides a nucleic acid prepared using the device according to the first aspect.

It will be appreciated that the device of the invention may be advantageously employed for other methods, for example methods of analysing an antibody-antigen binding reactions.

According to a fifth aspect the present invention provides a port for introducing a volume of a liquid sample into a fluid carrier stream flowing through a continuous flow tube having an outlet and a common inlet into which said carrier stream and said liquid sample are both introduced, said port comprising: a reservoir for continuously supplying said inlet with said fluid carrier, said reservoir adapted to maintain a substantially constant level of fluid carrier above said inlet and being fluidly engageable with said inlet of said continuous flow tube such that, in use, said fluid carrier stream and said liquid sample are drawn through said continuous flow tube when said reservoir is at substantially atmospheric pressure and when said fluid carrier is chosen such that its properties are sufficient to maintain the physical shape of the liquid sample introduced therein.

Preferably the liquid sample is an aqueous sample and the fluid carrier is a hydrophobic liquid. The fluid carrier can be suitably an oil such as a silicon oil. A sample port according to claim 3, wherein the hydrophobic liquid is an oil.

According to a sixth aspect the present invention provides a continuous flow apparatus comprising the sample port according to the fifth aspect.

Preferably the continuous flow apparatus is a thermocycling apparatus for performing nucleic acid amplification reactions. The preferred method of amplifying the nucleic acids is PCR.

According to a seventh aspect the present invention provides a method for introducing a volume of a liquid sample into a fluid carrier stream flowing through a continuous flow tube having an outlet and a common inlet into which said carrier stream and said liquid sample are both introduced, said method comprising the steps of: providing a port according to the fifth aspect; fluidly engaging said inlet of said continuous flow tube with said reservoir; introducing said fluid carrier into said reservoir and introducing said liquid sample into said fluid carrier, said fluid carrier chosen such that its properties are sufficient to maintain the physical shape of the liquid sample and such that said fluid carrier stream and said liquid sample are drawn through said continuous flow tube when said reservoir is at substantially atmospheric pressure.

According to an eighth aspect the present invention provides a method for introducing a volume of a liquid sample into a fluid carrier stream flowing through a continuous flow tube having an outlet and a common inlet into which said carrier stream and said liquid sample are both introduced, said method comprising the steps of: providing a port according to the fifth aspect; fluidly engaging said inlet of said continuous flow tube with said reservoir; introducing said fluid carrier into said reservoir; immersing a liquid sample dispenser into said fluid carrier contained in said reservoir; dispensing said liquid sample adjacent said inlet and optionally maneuvering said dispensed liquid sample with said liquid sample dispenser such that said dispensed liquid sample is introduced into said inlet and drawn through said continuous flow tube, said fluid carrier chosen such that its properties are sufficient to maintain the physical shape of the liquid sample and such that said fluid carrier stream and said liquid sample are drawn through said continuous flow tube when said reservoir is at substantially atmospheric pressure.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

Other than in the operating examples, or where otherwise indicated, all numbers expressing quantities of ingredients or reaction conditions used herein are to be understood as modified in all instances by the term "about". The examples are not intended to limit the scope of the invention. In what follows, or where otherwise indicated, "%" will mean "weight %", "ratio" will mean "weight ratio" and "parts" will mean "weight parts".

DEFINITIONS

In describing and claiming the present invention, the following terminology will be used in accordance with the definitions set out below. It is also to be understood that the terminology used herein is for the purpose of describing particular embodiments of the invention only and is not intended to be limiting. Unless defined otherwise, all technical and scientific terms used herein have the same meaning as commonly understood by one having ordinary skill in the art to which the invention pertains.

"Threaded" as in "threaded through" as used herein refers to the reaction tube being engaged with the heat exchangers. Thus, for example, the reaction tube is located within or wound through the tunnels of the heat exchangers, as clearly shown in FIG. 3. The term threaded is also intended to encompass embodiments wherein the reaction tube is reversibly captively received in surface grooves disposed on the surface of the heat exchangers i.e. "snap locked, or wound around the heat exchangers.

The term "tunnel" as used in the context of the present invention is intended to include configurations in which the opening is wholly within the wall of the heat exchangers, i.e. fully enclosed, as well as semi-circular openings, channels and/or grooves in or on the surface of the heat exchangers, thereby to receive the reaction tube in heat transfer communication. The terms "tunnel" and "groove" may be used interchangeably herein.

The term "nested" as used in the context of the present invention is intended to refer to a configuration of heat exchangers wherein at least one heat exchanger substantially surrounds another heat exchanger, or is placed substantially within the bounds of another. For example, in the preferred embodiment (see FIG. 1) a pair of rings are provided wherein the diameter of one ring is smaller than the other such that the small diameter ring may be placed within the bounds of the larger diameter ring.

The terms "drawn" and "drawing" in reference to the fluid carrier stream being drawn through the continuous flow tube when a suction force is applied to the continuous flow tube outlet are to be distinguished from "pushing", "propelling" or "pumping" the fluid carrier stream through the continuous flow tube when a pumping force is applied to the inlet. A pumping force is typically provided by the use of a high-pressure pump, such as a HPCL pump. In contrast, a suction force is typically applied by the use of a suction/aspirating/vacuum pump, optionally in conjunction with a vacuum bottle-type arrangement. For the purposes of the present invention a pumping force may be considered to be a positive force and a suction force a negative force. Furthermore, for the purposes of the present invention the reservoir is considered to be free from an applied pressure substantially greater than atmospheric pressure when the carrier fluid is being drawn through the continuous flow tube. A fluid may also be "drawn" through the continuous flow tube by the effects of gravity (when certain carrier fluids are used).

The term "atmospheric pressure" as used herein is intended to refer to an atmospheric pressure at substantially 101.325 kPa (i.e. 760 mm Hg) or its equivalent at different altitudes. However, the skilled person will appreciate that this term permits a degree of variation and that the number is not to be construed as a precise value.

Figure 2:
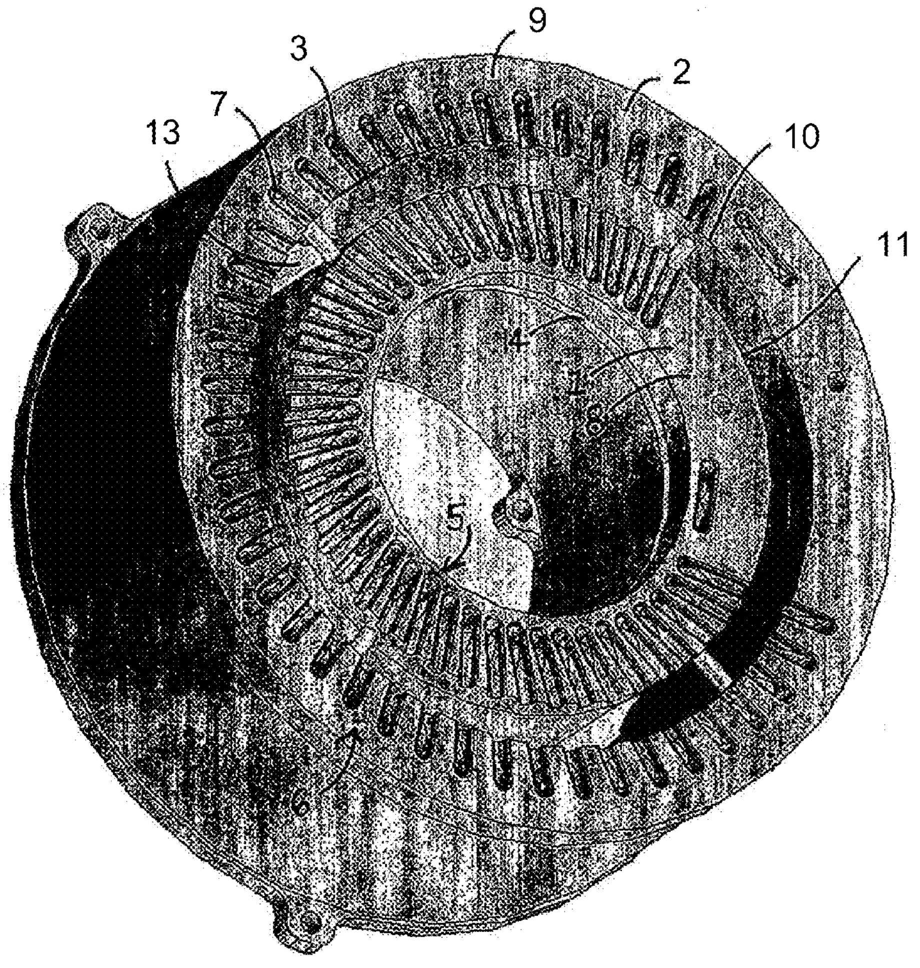
FIG. 2 is a perspective underside view of the thermocycler shown in FIG. 1.
Figure 3:
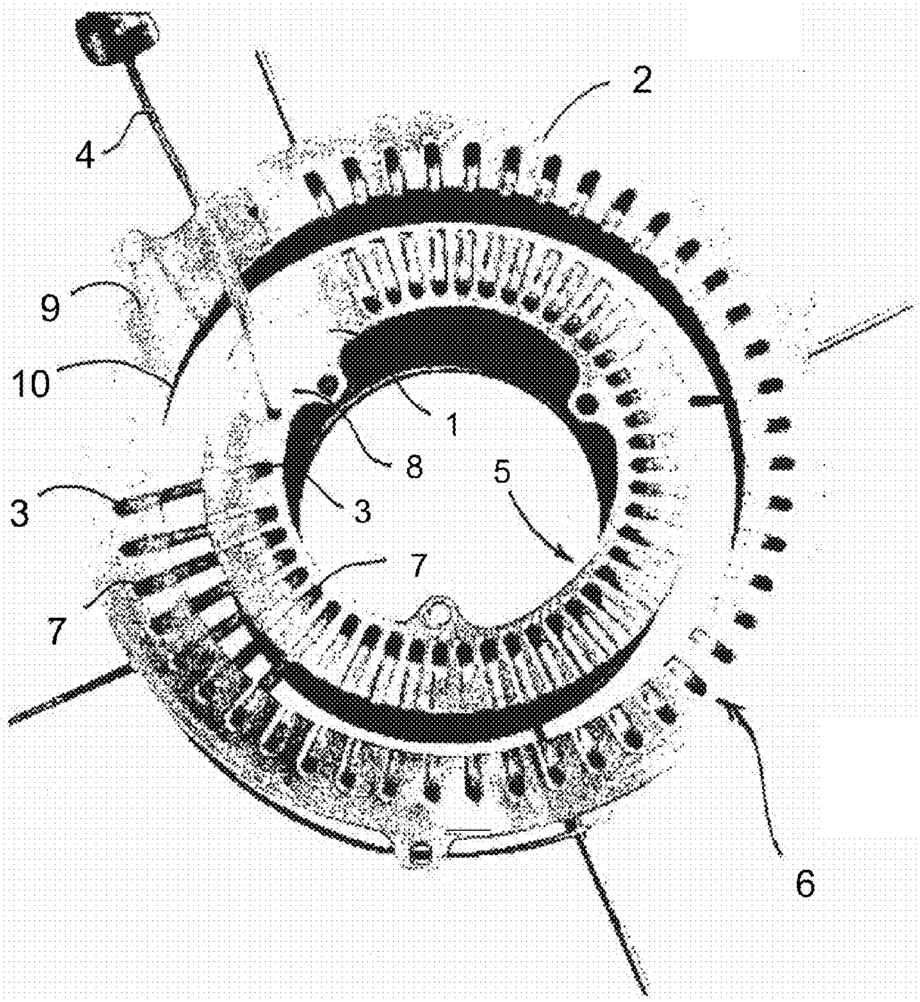
FIG. 3 is a top view of the thermocycler shown in FIG. 1, showing a portion of the reaction tube threadedly engaged with the tunnels.
Figure 4:
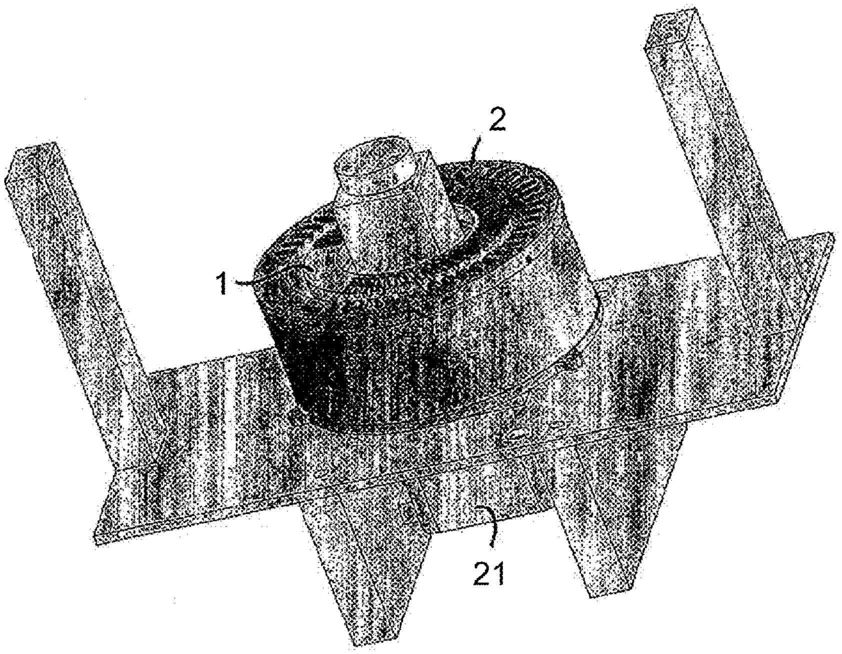
FIG. 4 is a perspective view of the thermocycler shown installed in PCR apparatus.
Figure 5:
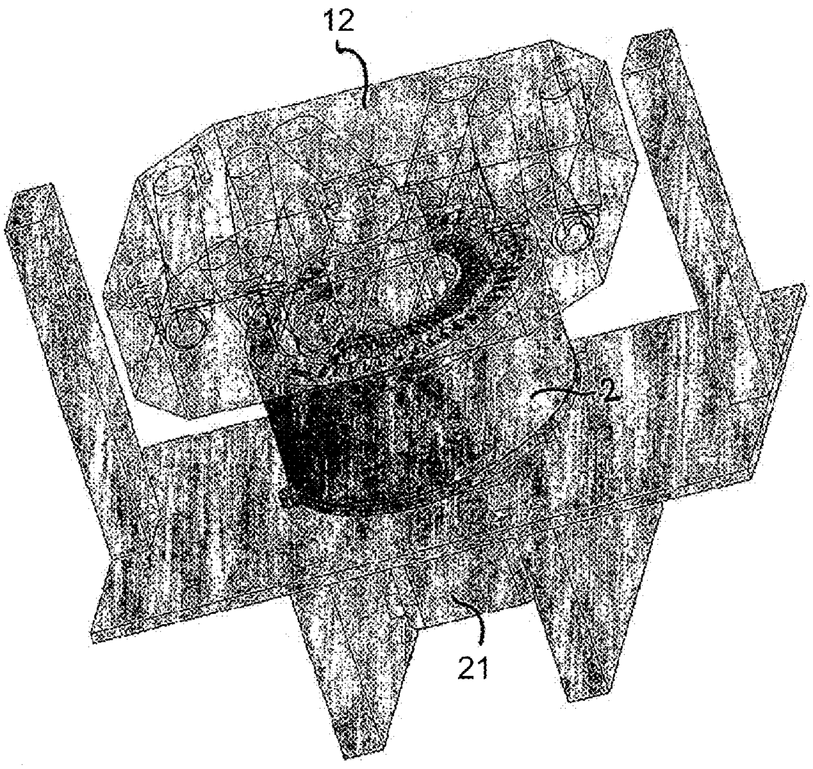
FIG. 5 is a view similar to FIG. 4 but including the rotatable scanning detector mounted above the heat exchanger rings.
Figure 6:
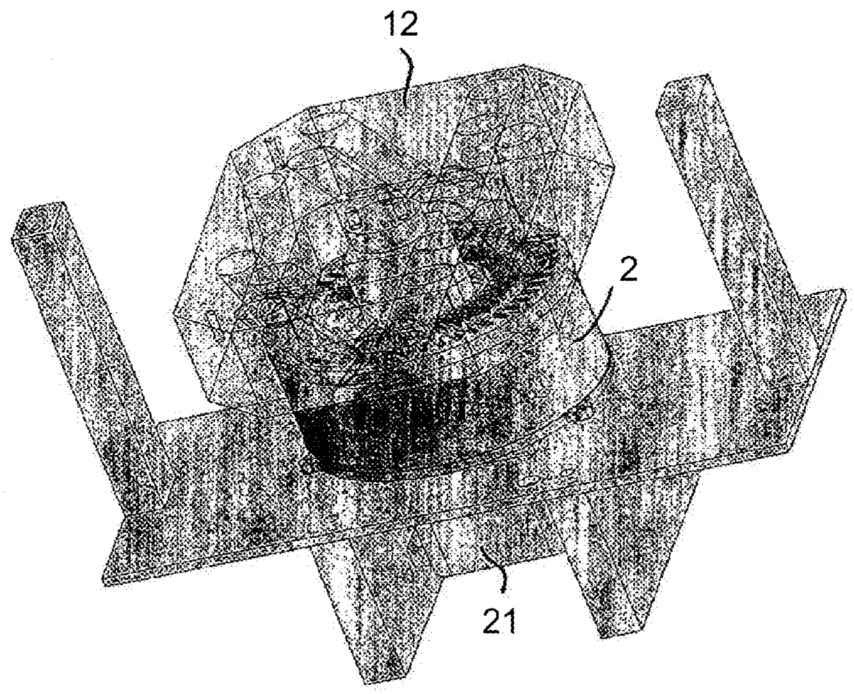
FIG. 6 is a view similar to FIG. 5 with the scanning detector shown rotated through 90°.
Figure 7:
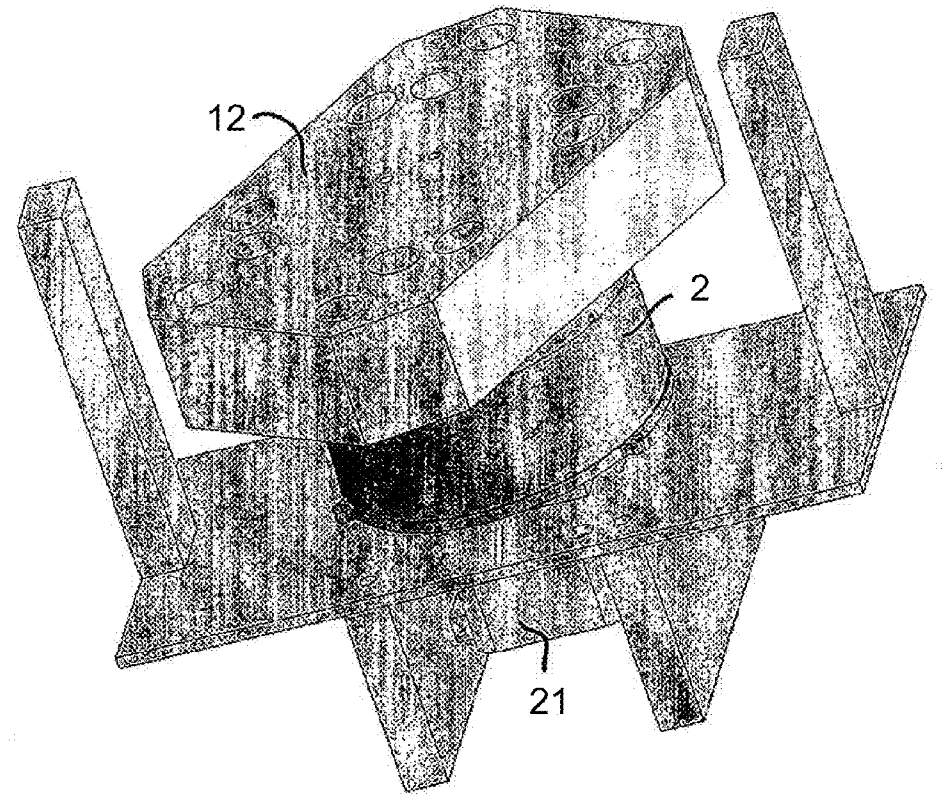
FIG. 7 is a view similar to FIG. 6 showing the detection channels.
Figure 8:
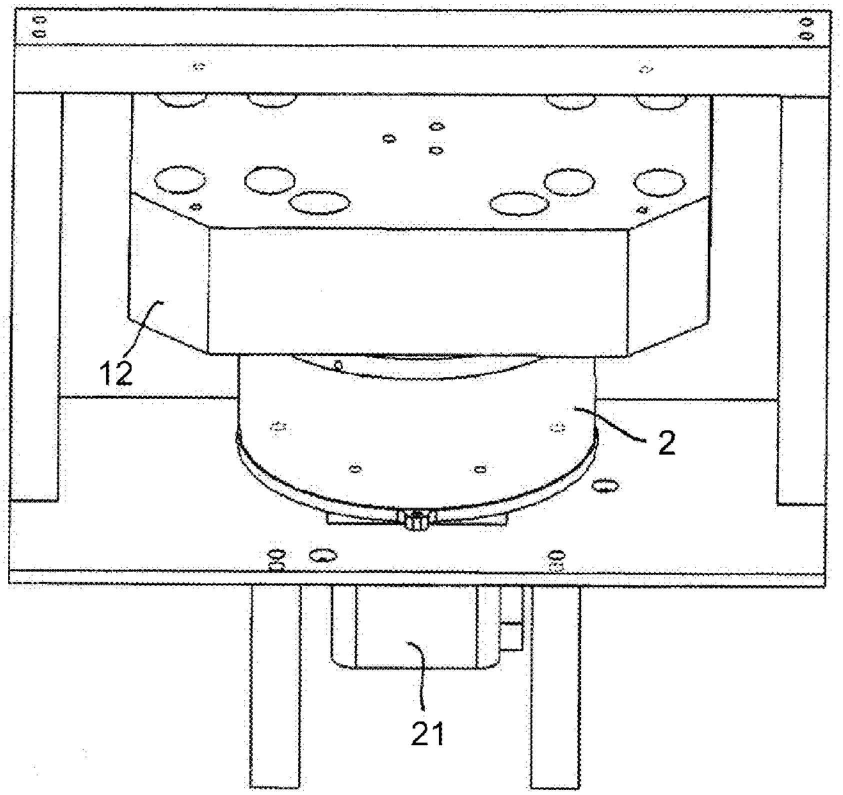
FIG. 8 is a view similar to FIG. 7.
Figure 9:
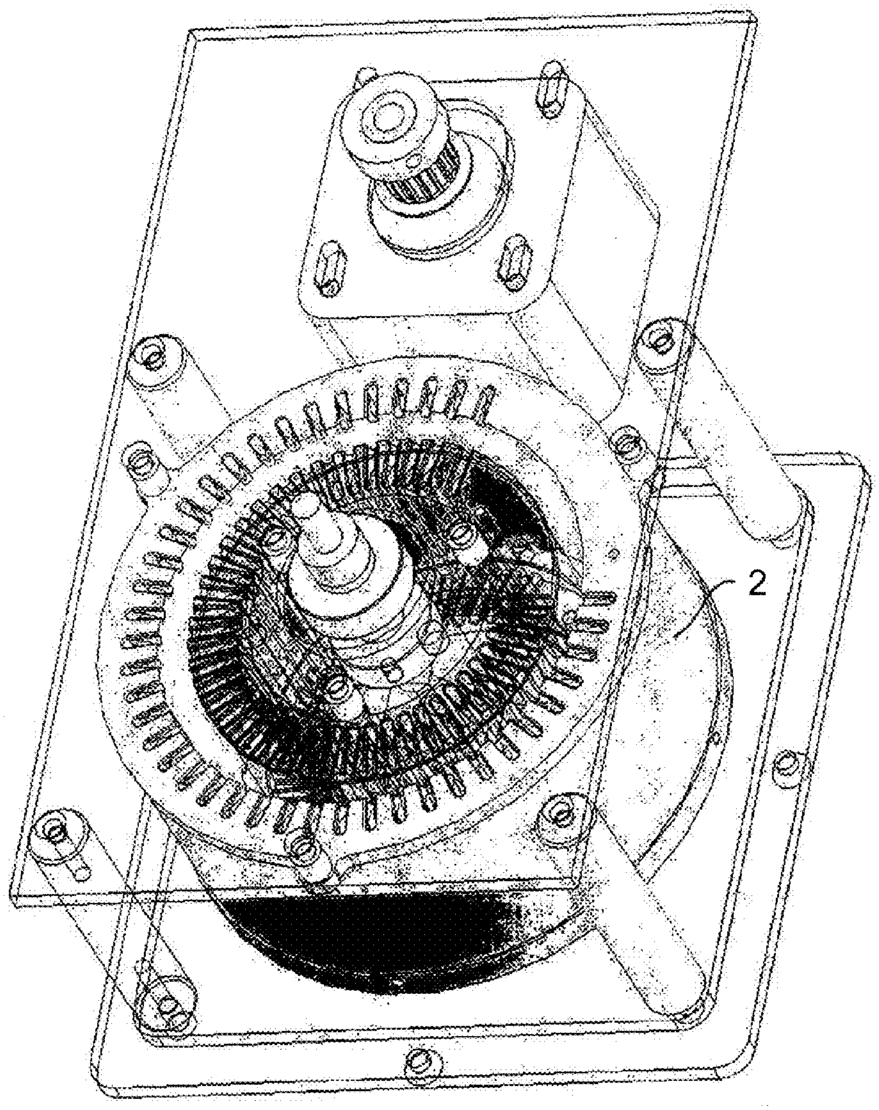
FIG. 9 is a perspective top view of the thermocycler shown installed in PCR apparatus with the inner heat exchanger ghosted-out for clarity.

Referring initially to FIGS. 1 to 3, the thermocycler includes a pair of discrete nested inner and outer right cylindrical heat exchanger rings 1 and 2 respectively. Each ring includes a plurality of tunnels 3 extending longitudinally through its wall. The number of tunnels may be between about 15 to 70, however in a typical configuration about 40 tunnels are provided. Each heat exchanger ring 1 and 2 is adapted to maintain a different predetermined temperature thereby to define two temperature zones. The temperature is maintained using heating and/or cooling means in the form of one or more resistance wires or Peltier devices (not shown). The temperature profile along the axial length of the heat exchanger rings 1 and 2 is maintained at a substantially constant value. The inner 1 and/or outer 2 of the heat exchanger rings may also be divided into a pair of discrete axially spaced sub-rings (not shown). Each of the sub-rings may be adapted to maintain a different predetermined temperature, thereby defining third and/or fourth temperature zones. The temperature zones may be maintained at any temperature but for nucleic acid amplification using PCR methodology they are typically chosen from about 95° C., about 60° C., and about 72° C. However, in alternative embodiments the thermocycler may include one or more further heat exchangers surrounding the outer heat exchanger for providing further temperature zones.

A reaction tube 4 is threadedly engaged in close fitting relationship with the tunnels 3 thereby to conduct heat from the heat exchanger rings 1 and 2 to a fluid in the reaction tube. The reaction tube is alternatingly threaded through successive tunnels of each ring 1 and 2 such that a fluid passing through the reaction tube 4 cyclically passes through the temperature zones.

Typically the reaction tube 4 is transparent and formed from an inert material such as Teflon, Tefzel or similar material, and the tube is preferably resilient to allow it to be threaded through the tunnels. Further, the internal surface of the tube 4 should be hydrophobic, to prevent adherence of sample, its contents or other potential contaminants.

Each ring 1 and 2 includes an array 5 and 6 respectively of mutually opposed reaction tube alignment formations 7 on their respective end surfaces 8 and 9. The formations 7 are disposed on the inner peripheral edge 10 of the outer ring 2 and on the outer peripheral edge 11 of the inner ring 1. The formations 7 are preferably longitudinally recessed radially extending slots for positioning the tube 4 such that the tube sits substantially flush with each end surface 8 and 9 of each ring 1 and 2.

The reaction tube 4 further includes an inlet port for introducing fluids into the tube and a delivery device for maintaining a constant flow through the tube (neither shown). Suitably the delivery device is in the form of a positive displacement pump which maintains a flow of about 100-200 μL/min through the reaction tube under a pressure of between about 70 to about 700 kPa. A backpressure may also applied at the end of the reaction tube and can be maintained between about 30 and 70 kPa, however the system also operates well without backpressure. If backpressure is applied the fluids are held under pressure to avoid or minimise degassing or vaporisation of the fluid stream.

The fluids introduced into the reaction tube include a sample to be analysed or reacted, reagents to be used in the analysis or reaction, and a carrier fluid. The carrier fluid separates a sample to be analysed or reacted from a following sample and substantially prevents contamination between samples. The carrier fluid is typically silicon oil but any synthetic oil which is devoid of biological contaminants such as RNA or DNA can also be used.

A typical sample for nucleic acid amplification may include DNA, oligonucleotide primers, deoxyadenosine triphosphate (dATP), deoxycytidine triphosphate (dCTP), deoxyguanosine triphosphate (dGTP), deoxythymidine triphosphate (dTTP), and at least one of a thermostable DNA polymerase, enzymatically active fragments thereof, an enzymatically active derivative thereof and a reverse transcriptase.

As will be appreciated, flow rate, the relative axial length of the heat exchanger rings 1 and 2 and/or the diameter of the reaction tube 4 can control the time the sample is maintained at the predetermined temperature. In a typical nucleic acid amplification reaction the time is sufficient such that the following reactions take place:

(a) denaturation of the DNA into its component strands;
(b) annealing of the oligonucleotide primers to complementary sequences in the DNA; and
(c) synthesis of new DNA strands.

These three steps are repeated as the sample is progressively pumped through the temperature zones until a desired level of amplification has been achieved. The number of amplification steps is proportional to the number tunnels provided in the thermocycler i.e. the number of times the sample passes through the designated temperature zones.

A marker reagent for monitoring the chemical reactions in the reaction tube may also be added to the sample. The marker reagent is typically a fluorescent dye but can be an intercalating dye, a chromogenic substrate, or oligonucleotide probes covalently bound to fluorescent moieties.

In further embodiments the thermocycler includes a C-shaped heat exchanger (not shown) surrounding the outer heat exchanger 2 for providing a post-melt on the amplified product. The circumferential gap of the C-shaped heat exchanger is typically about 20° and the heat exchanger includes a circumferentially varying temperature profile between about 70° C. to about 95° C. In a particularly preferred embodiment the tube 4 is disposed around the outer circumference of the C-shaped heat exchanger such that as the sample is pumped around the circumference it undergoes a melt profile. However, in a most preferred embodiment, the reaction tube 4 is held in a groove disposed on the face of the C-shaped heat exchanger.

In alternative embodiments, the thermocycler may include a scanning detector for detecting the marker reagent and thus monitoring the course of the reaction occurring in the reaction tube 4. In one configuration, as best shown in FIGS. 5 to 8 the scanning detector includes a rotatable unit 12 mounted above (or below) the rings 1 and 2 for directly scanning the tube 4 in the circumferential gap 13 between the heat exchangers, or the formations 7, or the groove disposed on the face of the C-shaped heat exchanger. For example, an incident light and detection system may be mounted on the edge of a rotating unit positioned above the heat exchanger rings 1 and 2. Four detection channels (LED/diode or a laser/diode combinations) may be mounted so up to 4 fluorophores can be multiplexed in one sample and all four channels can acquire data simultaneously. Optically coupled devices, such as IR diodes, along the axis of rotation may feed the data stream from the detectors to the main data processing unit, or data may be fed into the detectors. However, any wireless data transmission would be suitable. Melt data is collected from a "melting" channel 20 mounted on the rotatable unit 12.

The scanning detector is powered ideally by a small generator located in the rotating detector head. Alternatively, spinning brushes may be used. However, any means for powering the detector may be used, for example stepper motor 21.

Figure 10:
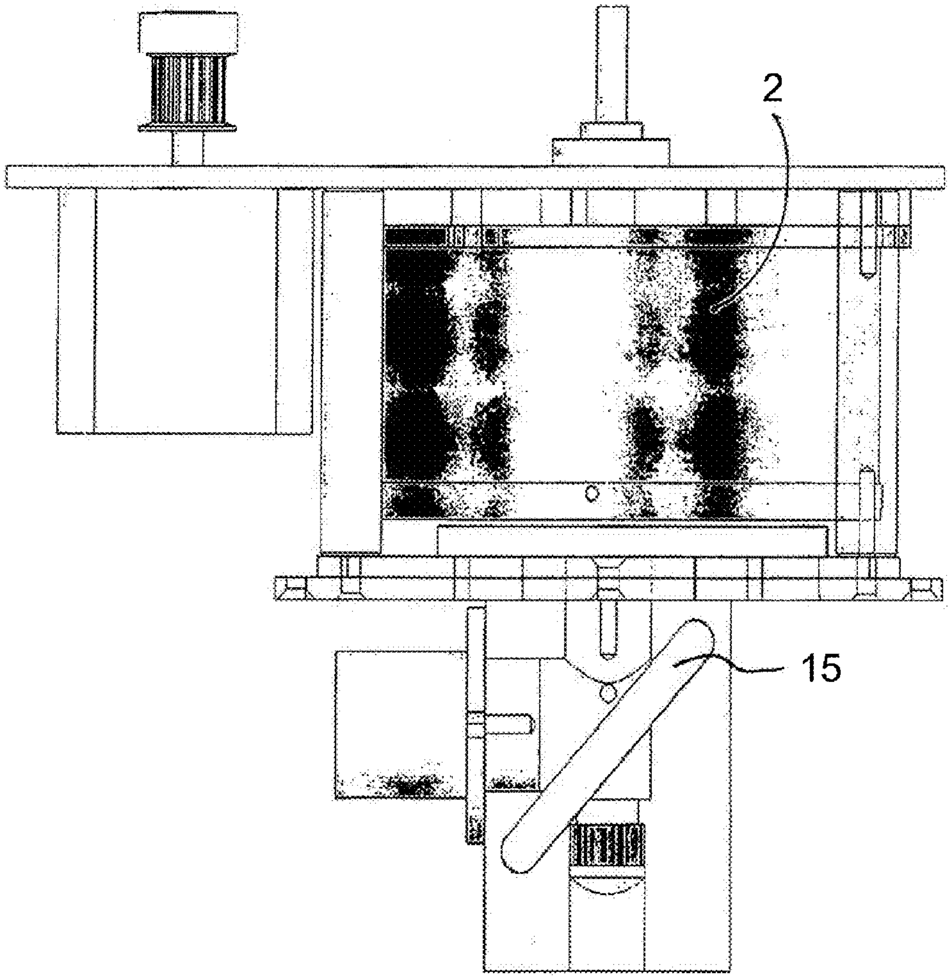
FIG. 10 is a side view of the PCR apparatus shown in FIG. 9.
Figure 11:
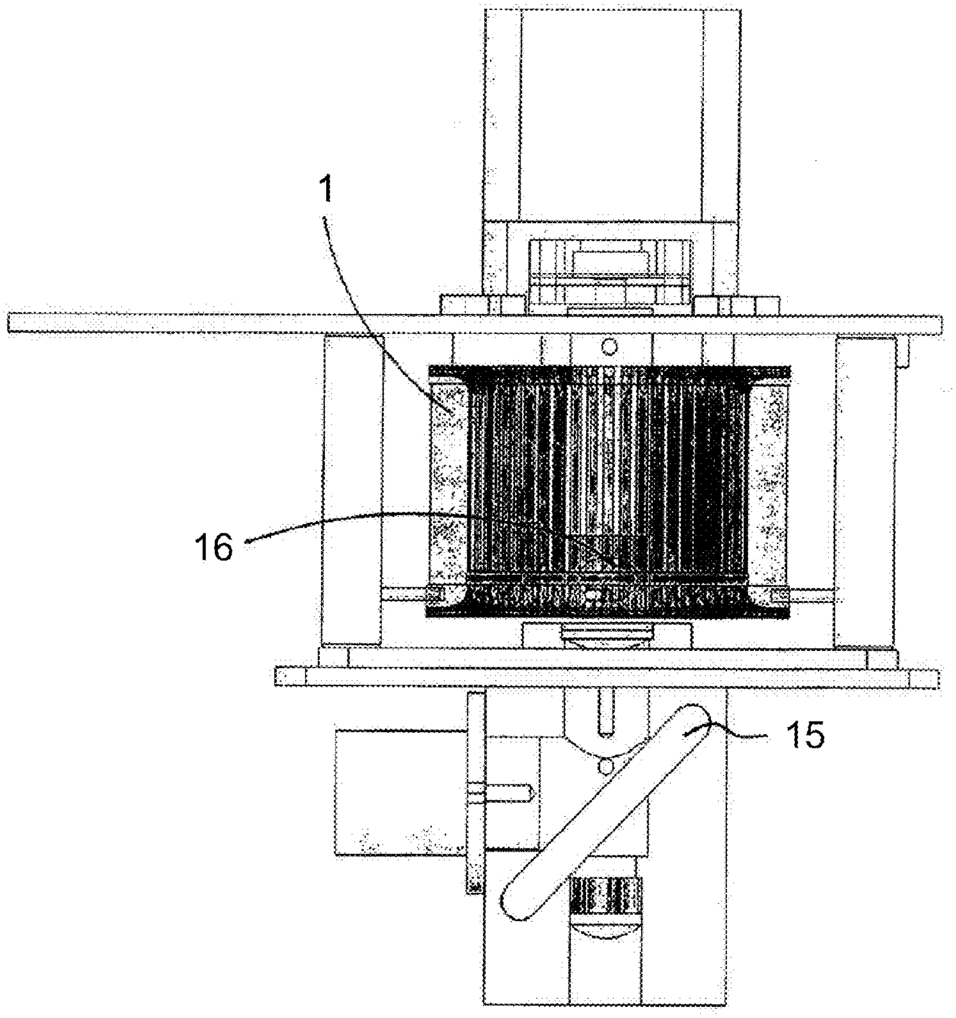
FIG. 11 is a view similar to FIG. 10 but having the outer heat exchanger removed for clarity and the inner heat exchanger ghosted-out to show the 45° rotating mirror and the slot for allowing optical measurement of the reaction tube.
Figure 12:
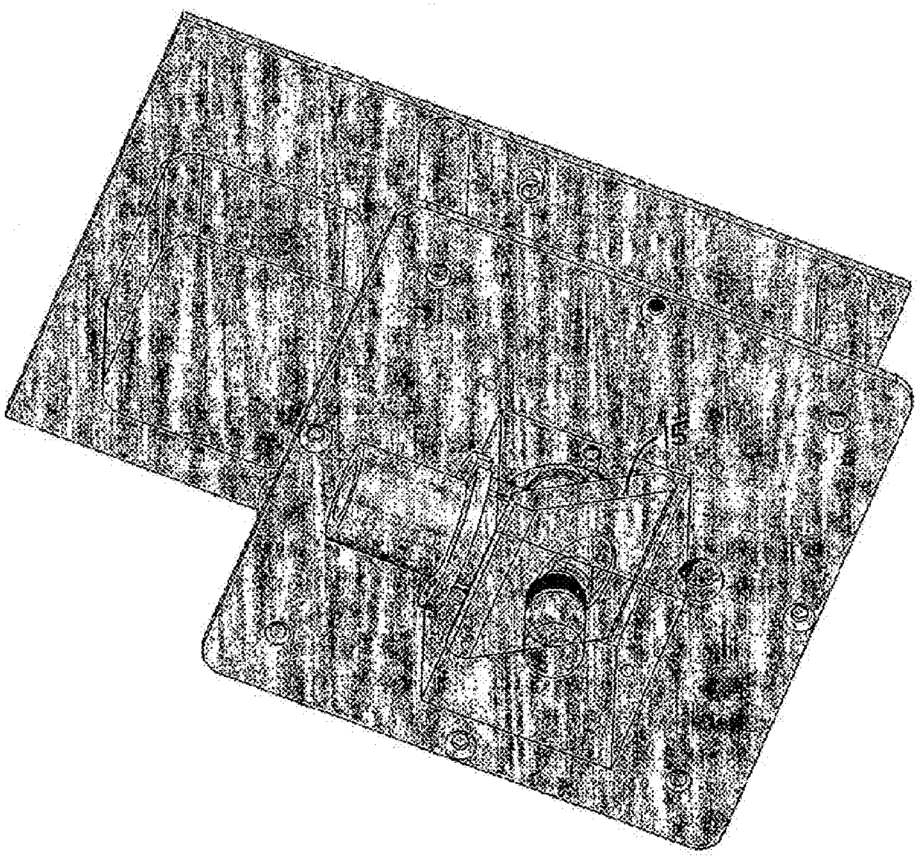
FIG. 12 is a perspective underside view of FIG. 9 showing the dichroic mirror and associated optics.
Figure 13:
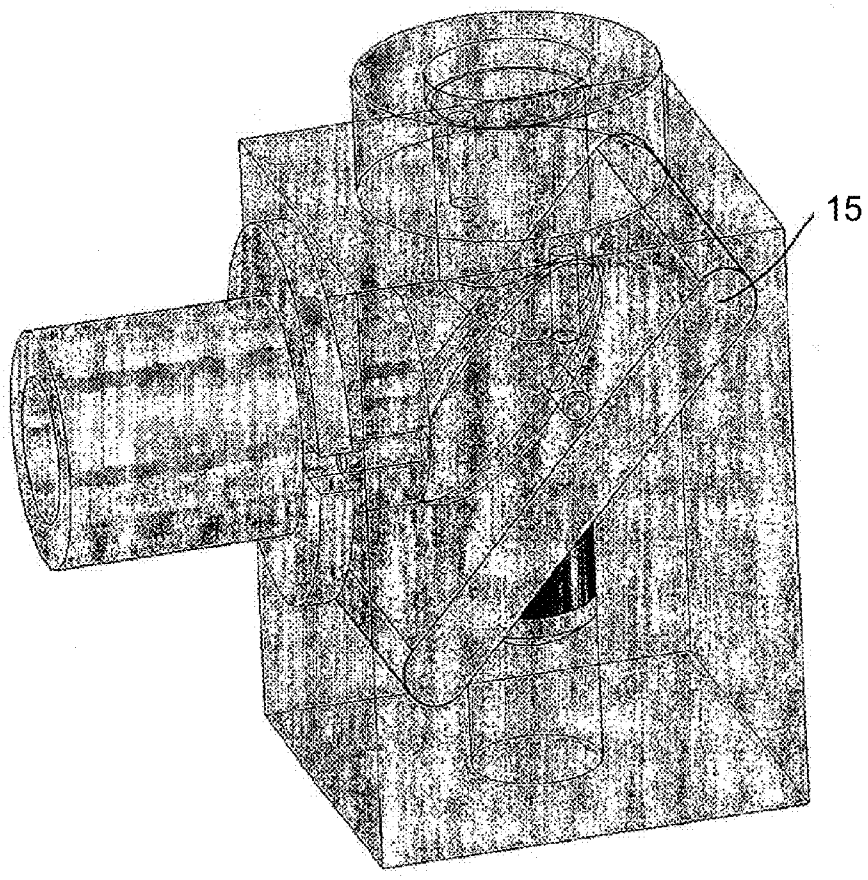
FIG. 13 is a perspective view of the dichroic mirror and associated optics shown in FIG. 12.
Figure 14:
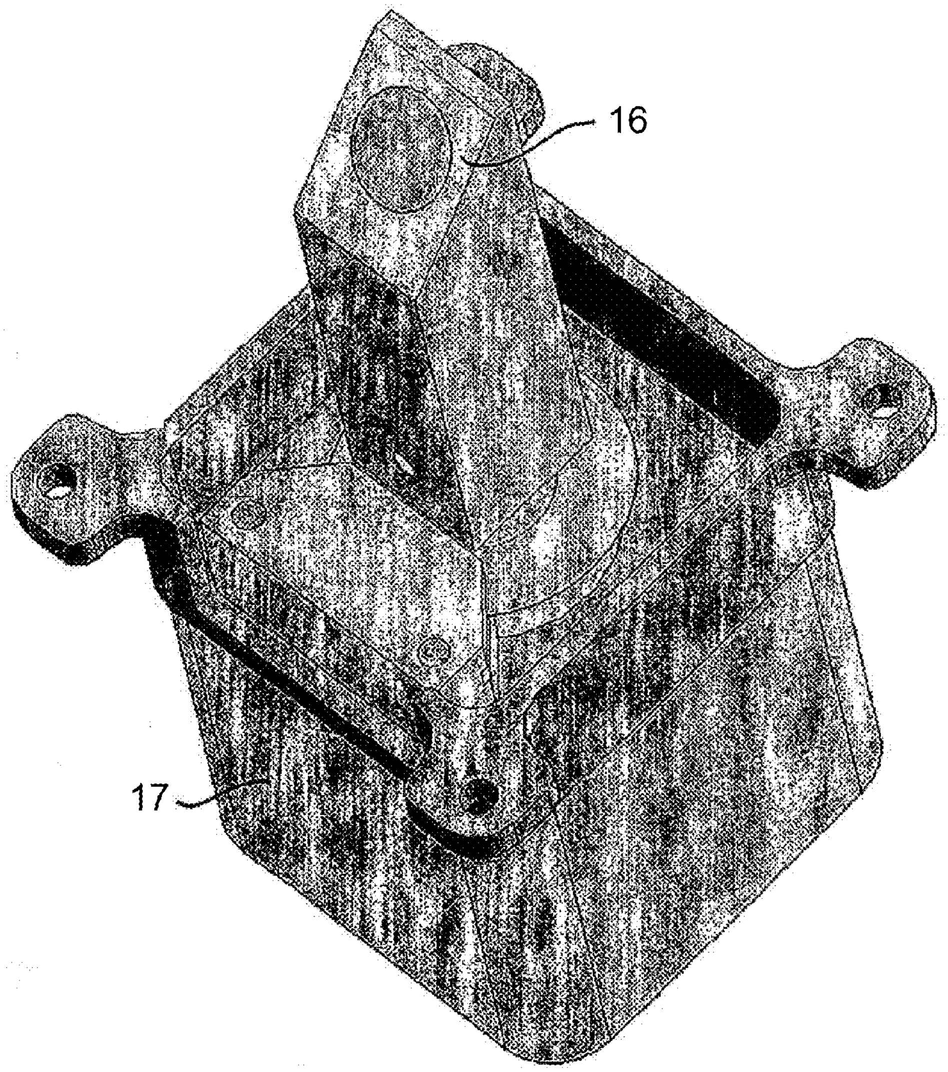
FIG. 14 is a perspective view of the 45° rotating mirror device.

In other configurations the inner heat exchanger ring includes an annular slot 14 for optically monitoring the reaction tube. As best shown in FIG. 10, a dichroic mirror 15 is axially mounted to one side of the PCR apparatus and an axially rotatable 45° mirror 16 is disposed within the inner of the rings thereby to detect the course of the reaction in the reaction tube through the annular slot 14. The scanning detector directs incident light along the axis of the thermocycler which is reflected onto each turn of the tube as the mirror 16 completes a single turn. The tube can be continuously scanned and each reaction be detected as it passes through the rotating light beam. Epifluorescent light passes back down the same optical path and passes through dichroic mirror 16 to a detector (not shown). Rapid rotation of the mirror by way of motor 17 allows the tubing to be continuously scanned, and each reaction to be detected as it passes through the rotating light beam. Fluorescence detection can be simultaneous with illumination or delayed using alternate illumination and detection scans.

In yet further embodiments, each scan of the scanning detector sends light intensity data to a data processing computer for sample identification. The number of bytes in each scan is identical allowing the data to be stored in a buffer, shifting the data down a row as each new scan is added. This creates a dynamic image of the tube fluorescence, stretched out onto a linear plane. A separate computer process then detects the samples by edge detection image analysis techniques. The data points within a sample "slug" or bolus are averaged and a fluorescence level is generated for that "slug" at that cycle number. These fluorescence levels and cycle numbers are then used to create a standard Rotor-gene REX file data format for analysis with Rotor-gene software, however any suitable data format is acceptable.

Turning now to the sample port assembly and its use with the continuous flow systems, as will be appreciated, the port according to the present invention allows the introduction of liquid samples into a continuous flow column without the need for prior art high-pressure injection ports or specialised injection apparatus. The port is relatively inexpensive compared to prior art high-pressure injection ports, has no moving parts and has no components that wear out (such as septa). Further, the port according to the present invention allows sample loading at atmospheric pressure with standard air displacement pipette tips which, since they are relatively inexpensive compared to needle-syringe injection apparatus, can be easily batch-sterilised and each tip discarded once used, thereby eliminating sample cross-contamination. In contrast, prior art needle-syringe injection apparatus must be cleaned/sterilised between sample injections. Further still, the "touch off" loading technique is "zero contact", meaning there is no contamination within the loading port. Yet further still, the port according to the present invention is particularly suitable for automatic sample loading by virtually any commercially available laboratory robotic system.

Preferably the fluid carrier is "drawn" (as opposed to "pushing" by pumping under high pressure) through the continuous flow tube by applying a suction force to the tube outlet. Drawing the fluid carrier stream through the continuous flow tube provides cost benefits compared to prior art devices since there is now no need for high-pressure pumps and, more importantly, no need for high pressure injection ports. However, in an alternative embodiment the fluid carrier is chosen such that the fluid carrier will be drawn through the continuous flow tube under the effects of gravity.

The suction force applied to the outlet of the continuous flow tube may be relatively easily provided by, for example, engaging the outlet of the continuous flow tube to a simple vacuum pump arrangement. For example, applying a vacuum of about 10 to 100 kPa to a 15-metre length continuous flow tube having a 1 mm internal diameter provides a flow of between about 50 to 500 μL/min. However, it will be appreciated that the flow rate is proportional to the internal diameter of the tube and/or the grade of oil and/or the amount of vacuum applied to the tube outlet. The tube could even be gravity fed by appropriate choice of grade of oil and tubing internal diameter. The skilled person will appreciate that other vacuums and flow rates can be provided according to the particular application. Preferably the vacuum should be controlled to maintain an even flow rate through the continuous flow tube.

Preferably the reservoir is open to, or held at atmospheric pressure, thereby providing a "zero pressure loading port". The preferred reservoir includes a centrally tapered base which is adapted to captively receive a continuous flow tube. However, in an alternative embodiment the reservoir may be pre-fitted with a length of conduit such that the outlet of the pre-fitted length of conduit may be fluidly engaged with the inlet of a pre-existing continuous flow tube. To ensure that no air is entrained in the continuous flow tube, the reservoir is configured such that the tube inlet is submerged within the volume of fluid carrier contained in the reservoir when the reservoir is fully charged with fluid carrier. The tube inlet is preferably substantially vertically configured to receive a liquid sample from above. Preferably a portion of the continuous flow tube intrudes into the reservoir such that the continuous flow tube inlet is disposed at about the centre of the height of the volume of fluid carrier contained in the reservoir when the reservoir is fully charged with fluid carrier. A suitable pump, such as a peristaltic pump, supplies the reservoir with fluid carrier and an optical sensor maintains pre-determined fluid level by controlling the rate of addition of fluid carrier into the reservoir. Alternatively, a weir-type arrangement may be provided for maintaining the fluid level. However, other arrangements will be apparent to the person skilled in the art providing that the reservoir is sufficiently maintained with fluid carrier at substantially atmospheric pressure.

A liquid sample may be introduced into the continuous flow tube by firstly positioning the tip of a sample dispenser, such as the tip of a pipette, just above the continuous flow tube inlet, and slowly dispensing the liquid sample. Preferably the liquid sample is about 20 μL. However, the liquid sample may be as small as 1 μL or as large as 50 μL. Due to surface tension effects the aqueous liquid sample dispensed into the hydrophobic oil carrier is substantially spherical in shape. Optionally the tip of the pipette remains in contact with the sphere of liquid sample to assist in maneuvering the sphere to the continuous flow tube inlet and prevent it from "falling away" to the wall of the reservoir. Since there is a flow of fluid carrier into the continuous flow tube inlet the sphere of liquid sample can then be "touched off" into the inlet from where it will be drawn into the continuous flow tube by the suction force applied to the outlet. It will be appreciated that a plurality of liquid samples may be introduced into the continuous flow tube at timed intervals. The liquid sample may be the same or different samples. Preferably, although not necessarily required, an intervening "wash" fluid is added between samples. To explain, a preferred sample loading comprises the following sequence: wash-sample-wash-sample-wash-etc. Of course each wash/sample fluid are separated by carrier fluid. This sequence reduced sample cross-contamination since any portion of the sample which may become dislodged is "caught" by the wash fluid and not by the preceding sample. Preferably the wash fluid is water.

The sample port of the present invention is particularly suitable for high throughput automated systems. In an embodiment of the present invention the sample port may be charged with a plurality of sequential samples (and wash fluid doses if required) by way of a robotic sample handling system. In other embodiments of the sample port for high throughput applications, a plurality of continuous flow tubes may be provided. The continuous flow tube inlets are preferably spaced into an array within the reservoir. This embodiment is also conducive for robotic sample handling whereby a robotic system can introduce a plurality of liquid samples into the plurality of continuous flow tube inlets. Alternatively, the array of continuous flow tubes may merge downstream in a parallel configuration into a single continuous flow tube thereby defining a "parallel" manifold. In this embodiment the liquid samples are loaded sequentially from one end of the manifold to the other thereby allowing the liquid samples to be evenly spaced as they are drawn into and travel through the continuous flow tube. However, in other embodiments the array of continuous flow tube openings may merge downstream into a single continuous flow tube in series thereby defining a "series" manifold. Advantageously, in this embodiment the liquid samples may be loaded simultaneously.

In an alternative aspect, a low-pressure sample loading port is provided for use in a high-pressure continuous flow system. In this aspect, a pair of spaced tubes are provided which are housed between a pair of spaced rotatable plates to define a rotatable stage. In one position, one of the tubes is open to the atmosphere whilst the other is in-line with the high-pressure continuous flow tube. The tube that is open to the atmosphere contains fluid carrier and may receive a liquid sample. Once a liquid sample is loaded the stage is rotated such that the tube open to the atmosphere is switched "in-line" leaving the other tube available to receive a subsequent liquid sample. The process is then repeatable. It will be appreciated that this port arrangement provides sample introduction via disposable tip and no needle-syringe apparatus is required since there is no piercable septum and hence reduced possibility of sample cross contamination.

It will be appreciated that the port according to the present invention will be adaptable to many types of continuous flow apparatus. Of course, a suction force will need to be applied to the outlet of the continuous flow tube to draw the fluids/liquids therethrough rather than "pushing" the fluid stream through via high-pressure pumping. However, since vacuum pumps are relatively common and inexpensive laboratory apparatus which can relatively easily be adapted to provide a suction force to the outlet of a continuous flow tube, the Applicant believes that the cost associated with modifying existing continuous flow systems with the apparatus of the present invention will be relatively small.

In one embodiment, the present invention is suitable for any continuous flow device operated with a suction force. For example, it may be adapted for use with the continuous flow devices described in PCT Publication No. WO 03/016558. According to WO 03/016558, a fluid carrier stream interrupted by a plurality of liquid samples is pumped under pressure through a continuous flow tube coiled about a cylindrical heat exchanger having a plurality of different temperature zones. The temperature zones are chosen to provide denaturation of nucleic acid into its component strands; annealing of oligonucleotide primers to complementary sequences in the nucleic acid; and synthesis of new nucleic acid strands. The liquid samples flowing though the continuous flow tube are subject to these varying temperatures in a cyclical fashion until a desired level of amplification has been achieved (amplification scaling with the number of times the continuous flow tube is coiled about the heat exchanger). These and similar prior art devices necessarily require the use of high pressure pumps to force the fluid carrier stream through the continuous flow tube and a high pressure injection port to introduce the liquid samples into the fluid carrier stream. This equipment is relatively complex, expensive, requires regular maintenance and skilled operators. In contrast, the present invention advantageously avoids the use of such high-pressure equipment by employing the novel port as described herein and drawing rather than pushing/propelling/pumping the fluid carrier stream through the continuous flow tube.

When conducting a PCR using a continuous flow system, the fluid carrier utilised is preferably devoid of biological contaminants, e.g. extraneous nucleic acids such as RNA or DNA, and is chosen to substantially prevent contamination between the liquid samples flowing through the continuous flow tube. However, in the present invention the fluid carrier is also preferably chosen to maintain the physical properties of the liquid sample. The applicant has found that silicone oils are particularly suitable for the present invention. Ideally the fluid carrier is a silicone oil having a viscosity of between about 5 to 50 centistokes. However, it will be appreciated that the oil viscosity is not limited to this range. Without wishing to be bound by theory it is believed that suitability of silicon oils is primarily due to the relatively uniform chain lengths. Thus, any oil of suitable viscosity and having these chain-length characteristics would be useful as a fluid carrier. The applicant has also observed that preferred silicone oils are those which provide a neutral buoyancy to the liquid sample, i.e. those having a density between about 0.95 to 0.99 g/cc. However, it will be appreciated that the oil density is not limited to this range.

Preferably the liquid sample is a mixture of components for a PCR experiment. For example, the liquid sample includes a sample to be analysed or reacted and reagents to be used in the analysis or reaction. Preferably the sample to be analysed or reacted is a nucleic acid such as DNA or RNA containing sample. Other components of the sample will typically include oligonucleotide primers, deoxyadenosine triphosphate (dATP), deoxycytidine triphosphate (dCTP), deoxyguanosine triphosphate (dGTP), deoxythymidine triphosphate (dTTP), and at least one of a thermostable DNA polymerase, enzymatically active fragments thereof, an enzymatically active derivative thereof and a reverse transcriptase.

The continuous flow tube is preferably substantially transparent, resilient and formed from an inert material having a hydrophobic internal surface. For example, a continuous flow tube formed from Teflon or Tefzel or similar material is preferred. However the continuous flow tube can be formed of any suitable material which will allow fluids to be drawn therethrough under a suction force. Preferably the internal diameter of the tube is between about 1 to 1.6 mm.

It will be appreciated that whilst the sample port of the present invention will be particularly suitable for a continuous flow PCR apparatus, the apparatus and method of the present invention is not limited to this field. For example, the present invention will be suitable for protein disassociation systems and isothermal reactions wherein the sample fluorescence is measured every cycle. However, the present invention is particularly suitable for robotic methods for reduced contamination loading of a sample into continuous flow systems.

Figure 18:
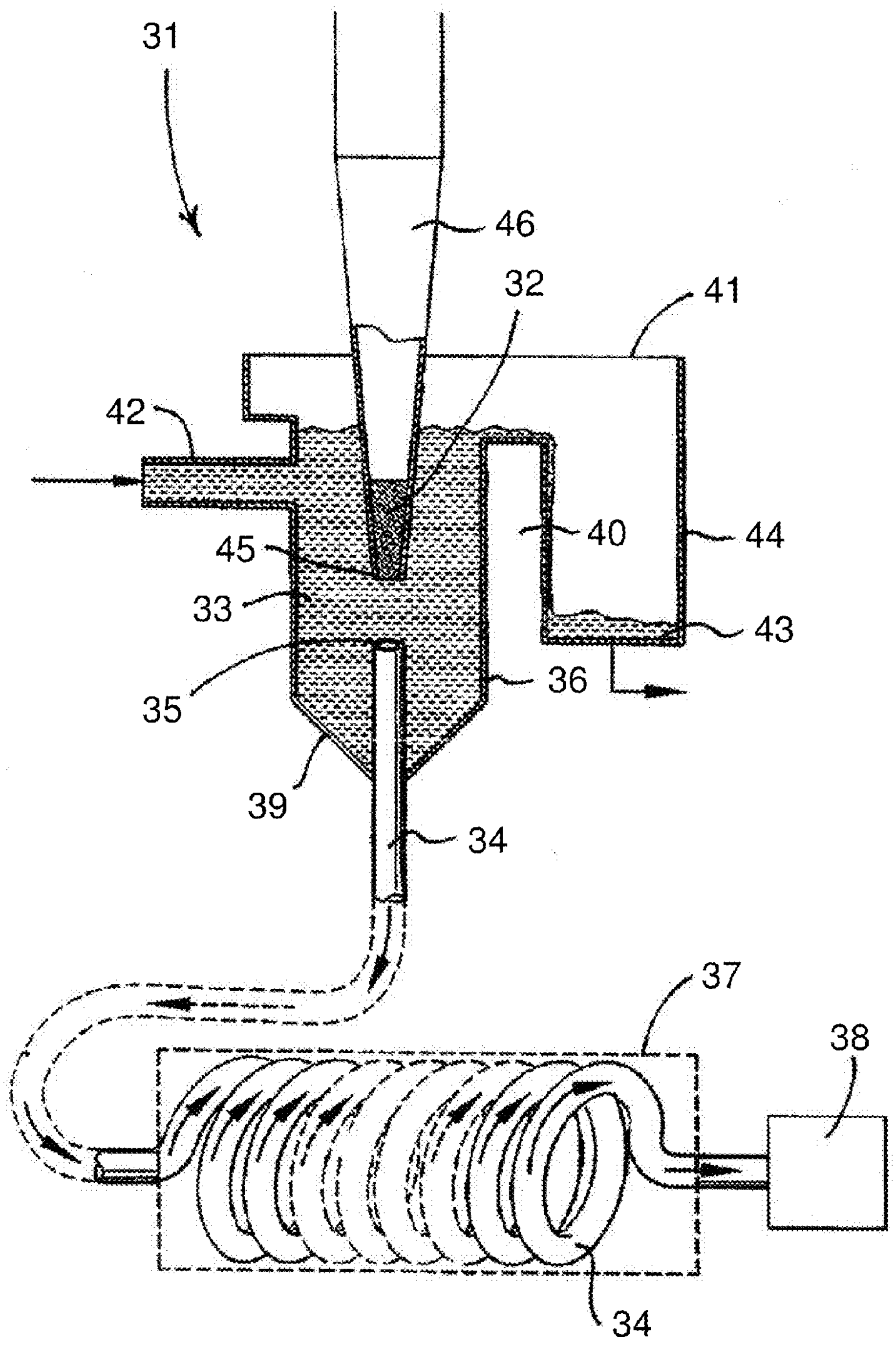
FIG. 18 is a side view of apparatus according to a fifth as sect of the present invention shown prior to introducing a liquid sample into the continuous flow tube inlet.

Reference will now be made to the drawings illustrating the sample port and its use with continuous flow systems, wherein like reference numerals refer to like parts throughout. Referring initially to FIG. 18, the present invention provides apparatus in the form of a port 31 and a method for introducing a volume of a liquid sample 32 into a fluid carrier 33 stream flowing into and through a continuous flow tube 34. The continuous flow tube 34 is preferably formed from Teflon and comprises an outlet (not shown) and a common inlet 35 into which the fluid carrier 33 stream and the liquid sample 32 are both introduced. The port 31 comprises a reservoir 36 for continuously supplying the inlet 35 with the fluid carrier 33. Since the reservoir 36 is preferably configured to be open to the atmosphere the fluid carrier 33 stream may be drawn through the continuous flow tube 34 by gravity or when sufficient suction force is applied to the outlet.

As discussed above, the present invention is particularly suitable for a continuous flow device for the amplification of nucleic acids using the PCR, and is also particularly suited to automated high throughput sample handling by robotic systems. Typically, in these devices a plurality of liquid samples 32 are introduced into the continuous flow tube 34 wherein each of the liquid samples 32 are separated by a volume of fluid carrier 33 to prevent contamination between liquid samples 32. In prior art devices this stream of liquid samples 32 and fluid carrier 33 is pumped through the continuous flow tube 34 and the continuous flow tube 34 is exposed to at least one temperature zone provided by a suitable heat exchanger 37. However, in this aspect present invention the stream of liquid samples 32 and fluid carrier 33 may be drawn through the continuous flow tube 34 by applying a suction force to the outlet of the continuous flow tube by, for example, a vacuum-bottle type arrangement 38. The liquid sample 32 may be a mixture of liquids for a PCR experiment and the fluid carrier 33 is a hydrophobic fluid such as an oil which is preferably devoid of extraneous biological contaminants, e.g. nucleic acids such as RNA or DNA.

Referring to FIG. 18 again, the reservoir 36 preferably includes a centrally tapered base 39. The continuous flow tube inlet 35 is submerged within the volume of fluid carrier 33 contained in the reservoir 36 and is vertically configured to receive a liquid sample 32 from above. A weir 40 is provided for maintaining the level of fluid carrier 33. The surface 41 of the reservoir 36 is open to atmospheric pressure and a pump (not shown), such as a peristaltic pump, supplies the reservoir 36 with fluid carrier 33 through inlet 42. The over-flow 43 of fluid carrier 33 in well 44 is returned to the pump for recycling.

Figure 19:
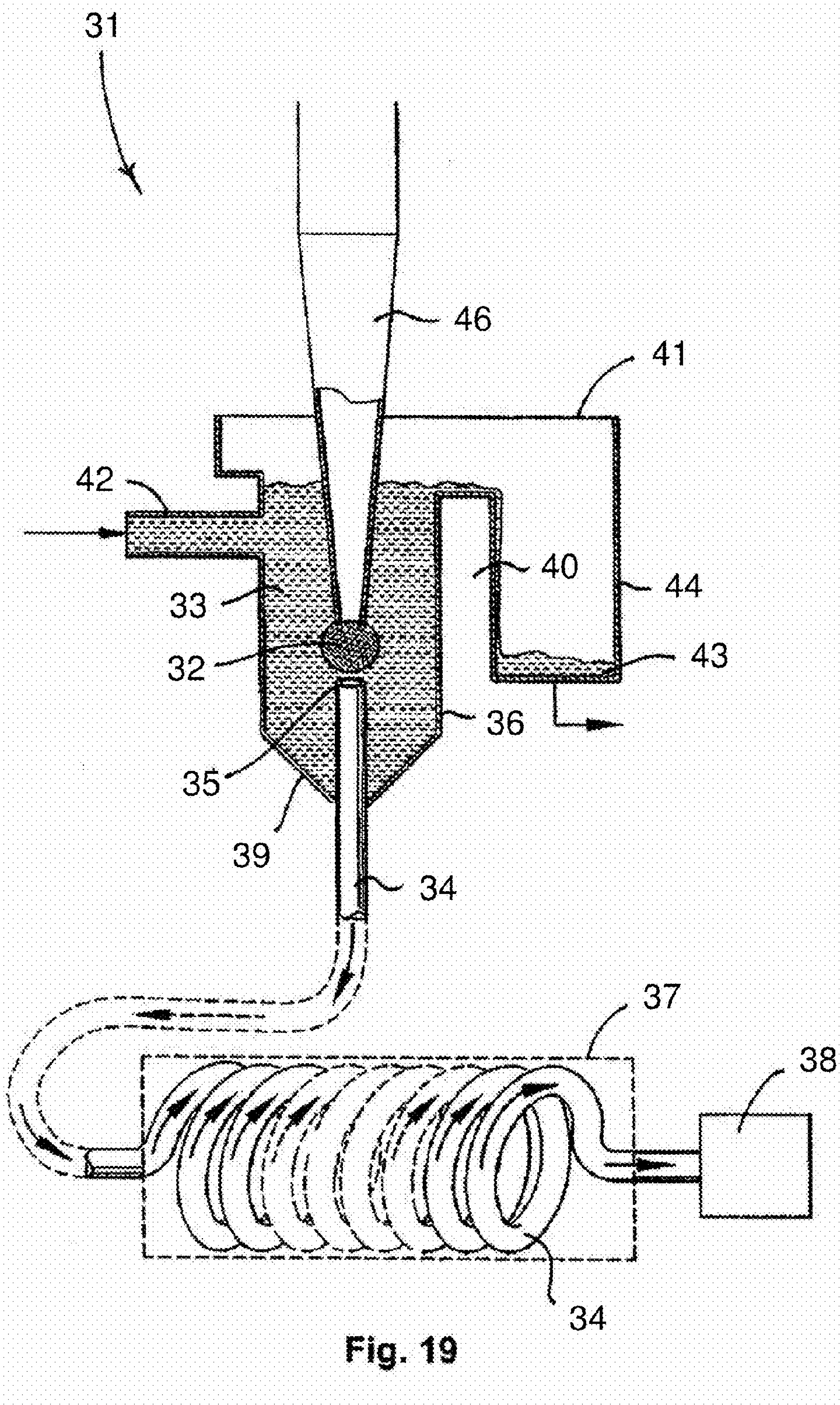
FIG. 19 is a view similar to FIG. 1 but showing the liquid sample introduced into the reservoir of fluid carrier.
Figure 20:
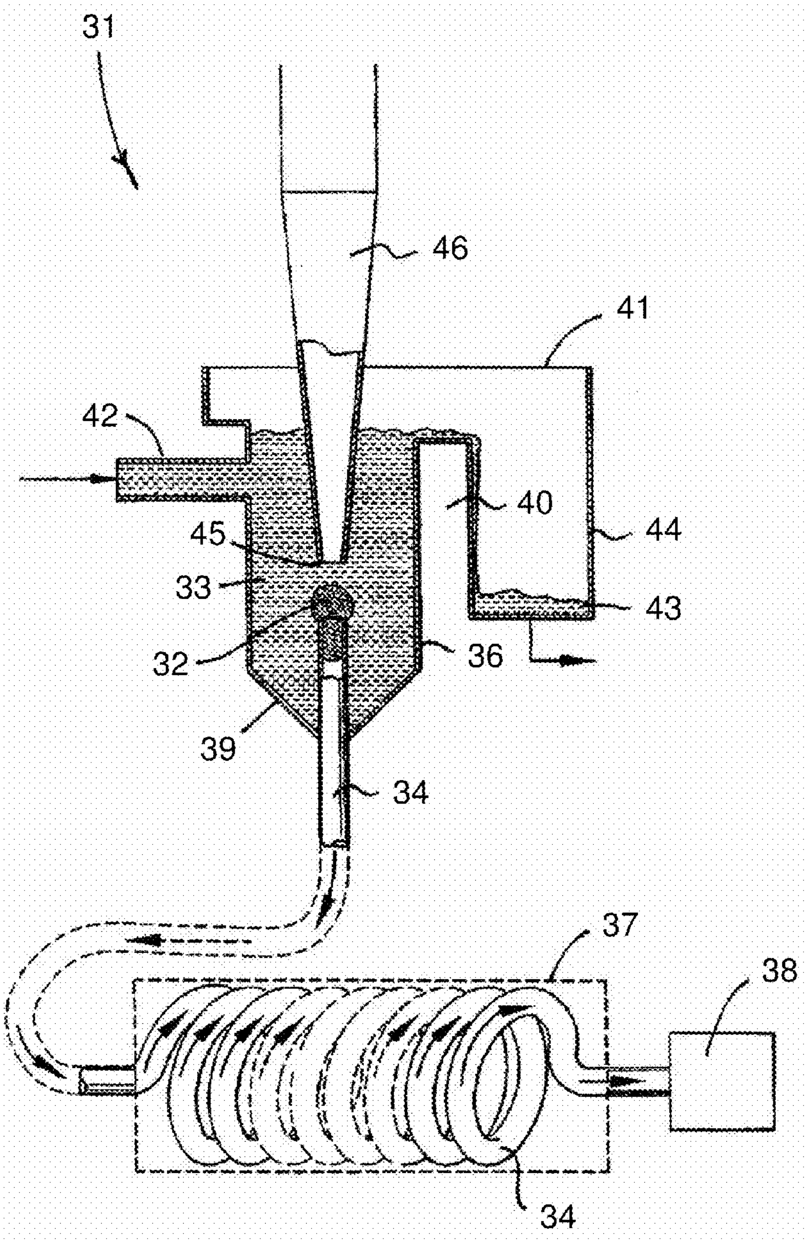
FIG. 20 is a view similar to FIG. 2 but showing the liquid sample drawn into the continuous flow tube inlet.

Referring now to FIGS. 18 to 20, the method of the invention comprises firstly engaging a continuous flow tube 34 to the reservoir 36 containing the fluid carrier 33 and applying a suction force to the outlet such that the fluid carrier 33 is evenly drawn through the continuous flow tube 34. A liquid sample 32 is then introduced into the continuous flow tube 34 by positioning the tip 45 of a pipette 46 above the continuous flow tube inlet 35 and dispensing about 10 μL of the liquid sample 32. The aqueous liquid sample 32 dispensed into the silicone oil 33 is substantially spherical in shape. Preferably the tip 45 of the pipette 46 remains in contact with the sphere of liquid sample 32 to assist in maneuvering the sphere to the continuous flow tube inlet 35 and prevent it from "falling away" to the walls of the reservoir 36. Since there is a flow of fluid carrier 33 into the continuous flow tube inlet 35 the sphere of liquid sample 32 can then be "touched off" into the inlet 35 (see FIG. 20) from where it is drawn into the continuous flow tube 34 by the suction force applied to the outlet.

As discussed above, whilst the fluid carrier 33 prevents contamination between liquid samples 32 flowing through the continuous flow tube 34, the present Applicant has determined that the fluid carrier 33 should also be chosen to maintain the physical properties of the liquid sample 32. To explain, the fluid carrier 33 is preferably silicone oil having a viscosity of between about 5 to 50 centistokes and a density of about 0.98 g/cc thereby providing neutral buoyancy to the liquid sample 32. The Applicant has found that the sphere of liquid sample 32 tends to "fall away" to the walls of the reservoir 36 and become adhered/lodged on the walls if the incorrect oil is used. Further, if the sphere descends too quickly it may be "caught" near the continuous flow tube inlet 35 and not be entirely drawn into the continuous flow tube 34.

Figure 21:
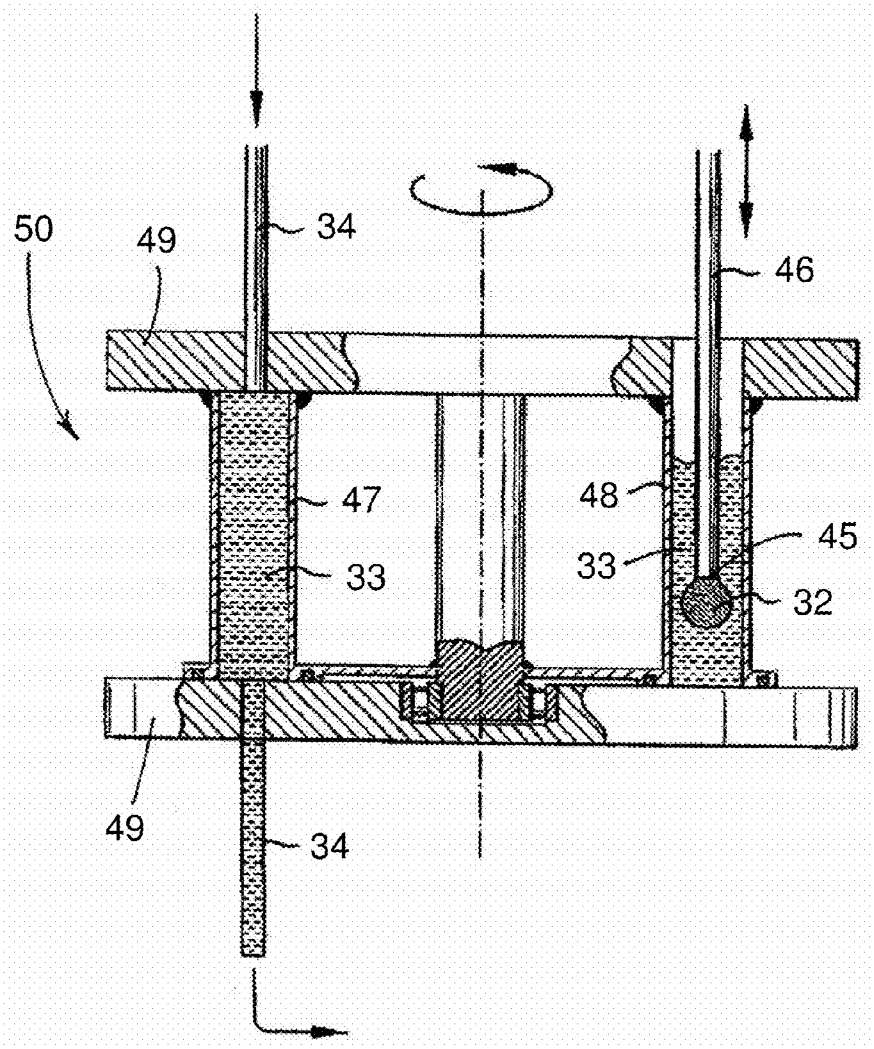
FIG. 21 is a side view of an alternative apparatus.

Referring now to FIG. 21, a pair of sample tubes 47, 48 are provided in an alternative port arrangement. The sample tubes 47, 48 are housed between a pair of spaced parallel plates 49 to define a rotatable stage 50. One of the sample tubes 47 is continuously replenished with fluid carrier 33 from a pump whilst the other sample tube 48 is free to receive a liquid sample 32 at atmospheric pressure. Once a liquid sample 32 is loaded into the sample tube 48 the tube 48 is then switched "in-line" by rotation of the rotatable stage 50, thereby introducing the liquid sample 32 into the continuous flow tube 34. The sample tube 47 "replaced" by sample tube 48 (that has just been switched "in-line") is thus available to receive a subsequent liquid sample 32.

In an alternate configuration for high throughput applications, a plurality of continuous flow tubes 34 may be provided for simultaneously conducting a plurality of nucleic acid amplifications. The continuous flow tube inlets 35 are preferably spaced into an array within the reservoir 36. This embodiment is conducive for robotic sample handling whereby a robotic system can introduce a plurality of liquid samples 32 into the plurality of continuous flow tube inlets 35. Alternatively, the array of continuous flow tubes may merge downstream in a parallel configuration into a single continuous flow tube 34 thereby defining a "parallel" manifold. In this embodiment the liquid samples 32 are loaded sequentially from one end of the manifold to the other thereby allowing the liquid samples 32 to be evenly spaced as they are drawn into and travel through the continuous flow tube 34. In other embodiments, the array of continuous flow tube openings 35 may merge downstream into a single continuous flow tube 34 in series, thereby defining a "series" manifold. As will be appreciated, in this embodiment the liquid samples 32 may be loaded simultaneously.

The sample port according to the present invention is easily adaptable to many types of continuous flow apparatus. Apart from the port itself, the only substantive change to these existing apparatus is the provision of a suction force to the outlet of the continuous flow tube, if gravity feeding is insufficient, to draw the fluids therethrough rather than "pushing" the liquid stream through via high-pressure pumping. The suction force, where required, can be supplied by a standard vacuum pump or the like.

The present invention will now be described with reference to the following examples which should be considered in all respects as illustrative and non-restrictive.

EXAMPLES

Example 1

Sample Injection (Positively Pressurized System)

An important aspect of the present invention is sample injection without contamination, i.e. the ability to completely separate samples as they pass through the device without the aqueous sample breaking up in the flow of oil, and without fluorescence from one sample contaminating the next. In practice it is important to wash the inside and outside of the stainless steel syringe, then inject the sample, followed by a further wash step. For example, a stainless steel needle having 300 mm length is mounted on a CAS robotics head and is used to collect and load samples. Preferably the internal volume of the needle is greater than the sample volume to minimize contamination. In these embodiments the internal volume of the needle is approx 8 μL and so up to a 5 μL sample can be safely loaded without the sample being drawn out the back of the needle and into the syringe barrel. The loading syringe system is purged with milliQ water and a sample is loaded into the needle as follows:

1) Load 2 μL oil
2) Load 5 μL sample
3) Wash outside of needle with "water bubbler"
4) Load 2 μL oil Oil is loaded from a static tube, however, in alternative embodiments an "oil bubbler" may be used to eliminate the need for the "water bubbler" wash of the outside of the needle.

5) Load 8 μL into the loading port of the system.
6) Remove needle from loading port.
7) Purge needle with 100 μL water to clean inside and outside of the needle.
8) Wait 15-30 seconds
9) Inject 20 μL of MilliQ water into the loading port.
10) Wait 15-30 seconds
11) Repeat 1)

Example 2

Real-Time Monitoring of Reaction Tube

Figure 15:
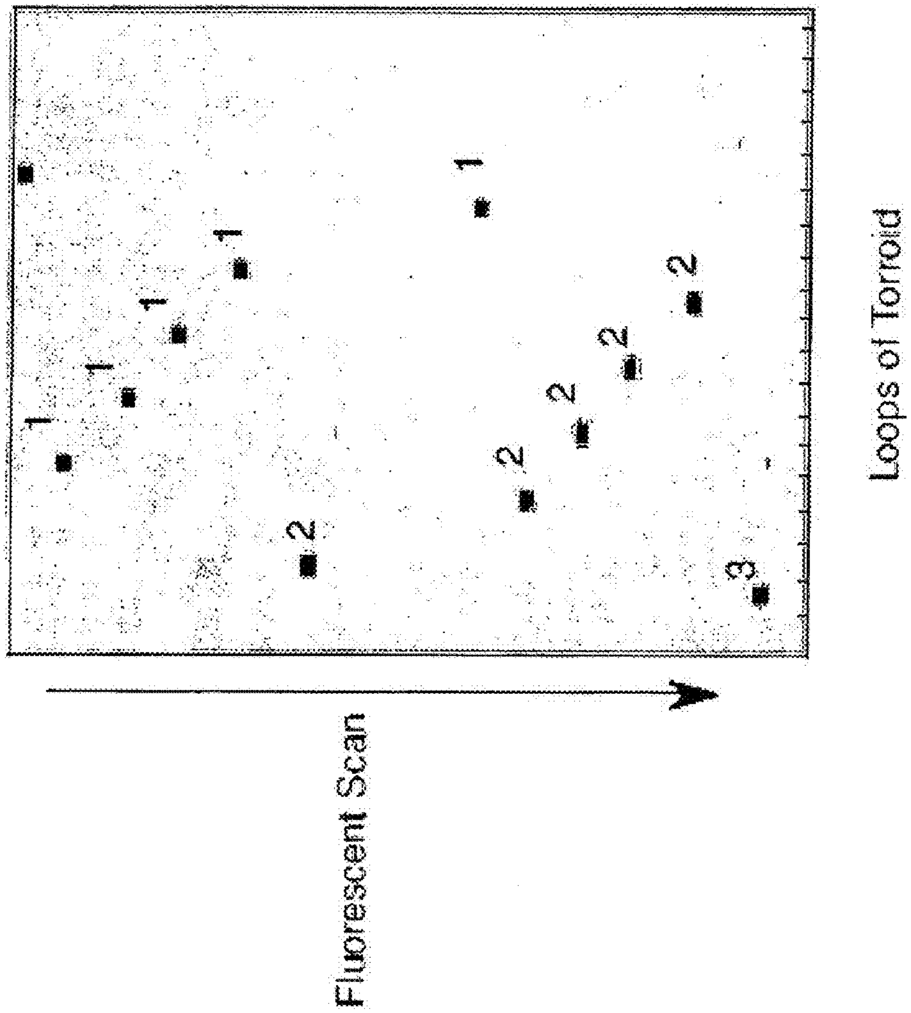
FIG. 15 is a raster image assembled from consecutive scans of samples passing through the reaction tubing.

Reference is made to FIG. 15 which provides a raster image assembled from consecutive scans of samples passing through the reaction tubing. A horizontal line, in which fluorescence is indicated by increased grayscale density, represents each scan. The numbers on the Figure identify three samples moving through the tubing. Only the last few turns of tubing are shown in this image after fluorescence in the sample has developed.

Figure 16:
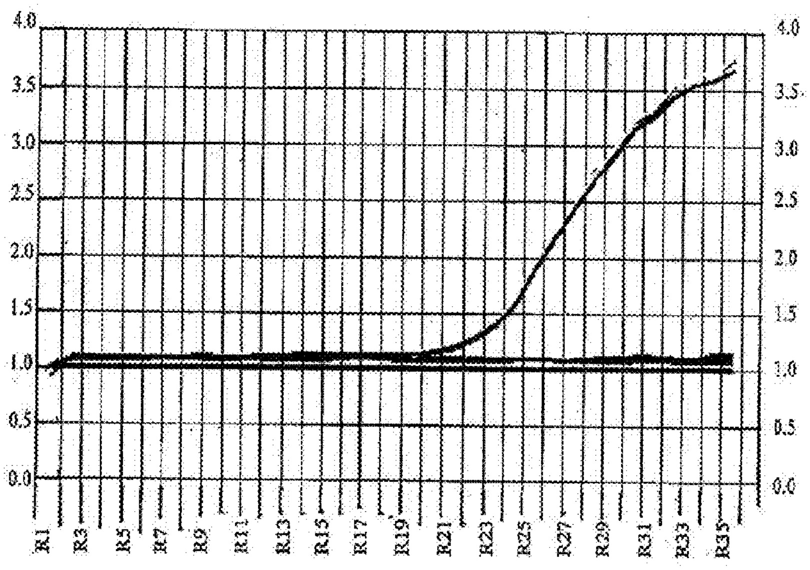
FIG. 16 is the data shown in FIG. 15 transformed into a graph of relative intensity vs turn number of the tubing.

The data show in FIG. 15 can be transformed into FIG. 16, in which relative intensity of the sample is plotted against the turn number of the tubing. The data shown in FIG. 16 allows a kinetic analysis of fluorescent changes in samples passing through flow device. In this particular example, samples C2, C4 and C6 contained DNA template for the specific amplicon used, and alternate samples C1, C3, C5 and C7 contained no template.

Example 3

DNA Melt-Detection Studies

Figure 17:
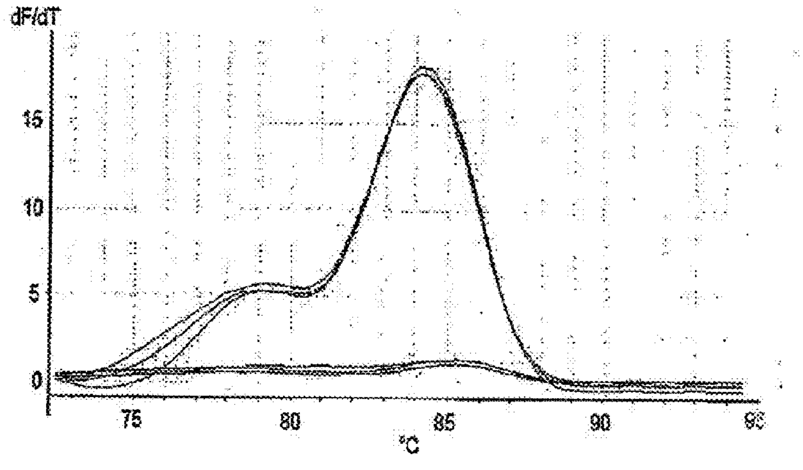
FIG. 17 shows DNA melting curves of samples analysed with template those curves exceeding the threshold) and without template (those not exceeding the threshold).

Reference is made to FIG. 17, which shows the DNA melting curves of samples analysed with template (those curves exceeding the threshold) and without template (those not exceeding the threshold). The temperature at which the product melts can be used as confirmation that substantially correct product has been formed.

Example 4

Atmospheric Pressure Sample Port ("Zero Contamination" Sample Injector)

Use of the sample port of the present invention enables an improved method for contamination-free sample application as well as the use of standard pipette tips for injecting the sample that can be easily sterilised and, as required, each tip discarded after sample application.

The sample port according to the present invention was fluidly engaged to ETFE (Tefzel) continuous flow tubing having internal diameter of 1.0 mm, external diameter of 1.6 mm and length approx. 15 m. Silicon oil was trailed having a similar density to water and 5 centistokes viscosity. This oil was sufficient to flow through the tubing under the effects of gravity and the oil flowed at 100 μL/min when the injection port was approx. 50 cm higher than the outlet of the continuous flow tube. When silicon oil with a similar density to water and a 50 centistokes viscosity was trailed a vacuum of 20 kPa needed to be applied to the tube outlet to achieve a 200 μL/min flow rate.

Commercial PCR buffers and TAQ's are supplied including a surfactant. This surfactant causes DNA to migrate from the aqueous phase to the oil phase during the flow process. Running positive and negative PCR controls results in contamination in the negative sample in about 20 cycles after the positive (i.e. 1 in a million). This level of contamination is not acceptable for PCR applications as typically a 1 in a billion level of amplification is achieved.

In a separate set of experiments each sample was loaded after a purge with milliQ water as follows:

1) Load 5 μL water

2) Load 5 μL sample

3) Repeat 1)

By injecting pure water samples in between every PCR reaction sample (i.e. "wash" fluid) contamination was not observed between a positive sample that amplified at cycle 3 and a negative sample that was run to 43 cycles. The samples injected were $H_2O$-positive-$H_2O$-negative-$H_2O$-positive . . . etc). Therefore, water injection between each sample provides a contamination level of better than 1 in a billion.

Although the invention has been described with reference to specific examples, it will be appreciated by those skilled in the art that the invention may be embodied in many other forms.

The invention claimed is:

1. A method for introducing a volume of a liquid sample into a fluid carrier stream flowing through a continuous flow tube having an outlet and a common inlet into which said carrier stream and said liquid sample are both introduced, said method comprising the steps of:

providing a sample port comprising a reservoir for continuously supplying said common inlet with said fluid carrier, and an inlet for supplying said reservoir with fluid carrier, said reservoir adapted to maintain a substantially constant level of fluid carrier above said common inlet and fluidly engageable with said common inlet of said continuous flow tube;

fluidly engaging said inlet of said continuous flow tube with said reservoir; and introducing said fluid carrier into said reservoir and introducing said liquid sample into said fluid carrier, wherein said fluid carrier is chosen such that its properties are sufficient to maintain the physical shape of the liquid sample and wherein said fluid carrier stream and said liquid sample are drawn through said continuous flow tube when said reservoir is at substantially atmospheric pressure.

2. A method according to claim 1, wherein the liquid sample is an aqueous sample.

3. A method according to claim 1, wherein the carrier fluid is a hydrophobic liquid.

4. A method according to claim 3, wherein the hydrophobic liquid is an oil.

5. A method according to claim 4, wherein the oil is a silicone oil or a silicone-based oil.

6. A method according to claim 1, wherein said reservoir is open to atmospheric pressure during use.

7. A method for introducing a volume of a liquid sample into a fluid carrier stream flowing through a continuous flow tube having an outlet and a common inlet into which said carrier stream and said liquid sample are both introduced, said method comprising the steps of:

providing a sample port comprising a reservoir for continuously supplying said common inlet with said fluid carrier, and an inlet for supplying said reservoir with fluid carrier, said reservoir adapted to maintain a substantially constant level of fluid carrier above said common inlet and fluidly engageable with said common inlet of said continuous flow tube;

fluidly engaging said inlet of said continuous flow tube with said reservoir;

introducing said fluid carrier into said reservoir;

immersing a liquid sample dispenser into said fluid carrier contained in said reservoir; and dispensing said liquid sample adjacent said inlet and manoeuvring said dispensed liquid sample with said liquid sample dispenser such that said dispensed liquid sample is introduced into said inlet and drawn through said continuous flow tube, wherein said fluid carrier is chosen such that its properties are sufficient to maintain the physical shape of the liquid sample and wherein said fluid carrier stream and said liquid sample are drawn through said continuous flow tube when said reservoir is at substantially atmospheric pressure.

8. A method according to claim 7, wherein said reservoir is open to atmospheric pressure during use.

9. A method according to claim 7, wherein the liquid sample is an aqueous sample.

10. A method according to claim 7, wherein the carrier fluid is a hydrophobic liquid.

11. A method according to claim 10, wherein the hydrophobic liquid is an oil.

12. A method according to claim 11, wherein the oil is a silicone oil or a silicone-based oil.

* * * * *